United States Patent
Sollanek

(10) Patent No.: US 9,419,462 B2
(45) Date of Patent: Aug. 16, 2016

(54) METHOD OF LASER WELDING THE HOUSING OF A RECHARGEABLE BATTERY

(71) Applicant: Stryker Corporation, Kalamazoo, MI (US)

(72) Inventor: Jeff Sollanek, Kalamazoo, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 14/826,753

(22) Filed: Aug. 14, 2015

(65) Prior Publication Data

US 2015/0357613 A1 Dec. 10, 2015

Related U.S. Application Data

(62) Division of application No. 14/031,380, filed on Sep. 19, 2013, now Pat. No. 9,142,992, which is a division of application No. 12/582,740, filed on Oct. 21, 2009, now Pat. No. 8,564,242, which is a division of application No. 11/551,335, filed on Oct. 20, 2006, now abandoned.

(60) Provisional application No. 60/729,338, filed on Oct. 21, 2005.

(51) Int. Cl.
*H02J 7/00* (2006.01)
*H02J 7/04* (2006.01)
(Continued)

(52) U.S. Cl.
CPC .............. *H02J 7/007* (2013.01); *H01M 2/1055* (2013.01); *H01M 2/34* (2013.01); *H01M 10/42* (2013.01); *H01M 10/425* (2013.01); *H01M 10/4257* (2013.01); *H01M 10/48* (2013.01); *H02J 7/0004* (2013.01); *H02J 7/0027* (2013.01); *H02J 7/0091* (2013.01); *A61B 17/141* (2013.01); *A61B 2017/00734* (2013.01); *H01M 10/44* (2013.01); *H01M 10/46* (2013.01);
(Continued)

(58) Field of Classification Search
USPC ......... 320/107, 110, 111, 112, 113, 114, 115, 320/132, 137, 134, 135, 136
See application file for complete search history.

(56) References Cited

U.S. PATENT DOCUMENTS 4,709,202 A 11/1987 Koenck et al.
5,018,227 A 5/1991 Canfield
(Continued)

FOREIGN PATENT DOCUMENTS

| EP | 1 471 593 A1 | 10/2004 |
|----|--------------|---------|
| GB | 2 317 510 A  | 3/1998  |
| JP | 2004-311257 A | 11/2004 |

OTHER PUBLICATIONS

Branson "IRAM™ Infrared Assembly Method", Nov. 2005.
(Continued)

*Primary Examiner* — Alexis A Boateng

(57) ABSTRACT

A rechargeable battery including a housing formed from two components formed from polyphenysulfone plastic. One housing component has a lip that is located inwardly of the other housing component. The housing components are further formed so that photonic energy at a select wavelength passes through the outer component and is absorbed by the lip of the second component. Once a rechargeable cell is placed in in one of the housing components, the housing components are placed together so the lip of the second component abuts an inner surface of the first component. Photonic energy at the select wavelength is directed to the joint between the components. The photonic energy passes through the first component and heats the lip of the second component. The heat causes the lip to melt. The melting plastic forms a hermetic weld between the housing components.

23 Claims, 28 Drawing Sheets

(51) Int. Cl.
*H01M 2/10* (2006.01)
*H01M 2/34* (2006.01)
*H01M 10/48* (2006.01)
*A61B 17/00* (2006.01)
*A61B 17/14* (2006.01)
*H01M 10/42* (2006.01)
*H01M 10/44* (2006.01)
*H01M 10/46* (2006.01)

(52) U.S. Cl.
CPC .. *H01M 2010/4271* (2013.01); *H01M 2200/00* (2013.01); *H02J 7/0042* (2013.01); *H02J 2007/0095* (2013.01); *Y10T 29/4911* (2015.01)

(56) References Cited

U.S. PATENT DOCUMENTS

| | | | |
|---|---|---|---|
| 5,554,154 | A | 9/1996 | Rosenberg |
| 5,608,306 | A | 3/1997 | Rybeck et al. |
| 5,734,253 | A | 3/1998 | Brake et al. |
| 5,754,027 | A | 5/1998 | Oglesbee |
| 5,754,029 | A | 5/1998 | Mann et al. |
| 5,893,959 | A | 4/1999 | Muellich |
| 5,895,440 | A | 4/1999 | Proctor et al. |
| 5,977,746 | A | 11/1999 | Hershberger et al. |
| 6,018,227 | A * | 1/2000 | Kumar ............... H01M 10/4257 320/106 |
| 6,169,387 | B1 | 1/2001 | Kaib |
| 6,184,655 | B1 | 2/2001 | Malackowski |
| 6,208,117 | B1 | 3/2001 | Hibi |
| 6,396,242 | B2 * | 5/2002 | Choi ..................... H02J 7/0042 320/113 |
| 6,456,043 | B1 * | 9/2002 | Finger ................... H02J 7/0032 320/134 |
| 6,504,344 | B1 | 1/2003 | Adams et al. |
| 6,597,152 | B1 | 7/2003 | Jacobs et al. |
| 6,913,087 | B1 | 7/2005 | Brotto et al. |
| 7,453,234 | B2 | 11/2008 | Phillips et al. |
| 7,471,066 | B2 | 12/2008 | Ambrosio et al. |
| 7,859,220 | B2 * | 12/2010 | Bushong ............... H02J 7/0045 320/107 |
| 2001/0020838 | A1 | 9/2001 | Malackowski |
| 2002/0000786 | A1 | 1/2002 | Choi et al. |
| 2002/0175655 | A1 * | 11/2002 | Huykman ........... G01R 31/3658 320/116 |
| 2003/0137279 | A1 | 7/2003 | Baur |
| 2004/0104709 | A1 | 6/2004 | Yamaji et al. |
| 2005/0017679 | A1 | 1/2005 | Tashiro |
| 2005/0017686 | A1 | 1/2005 | Sakakibara et al. |
| 2005/0024022 | A1 | 2/2005 | Howard et al. |
| 2005/0225301 | A1 * | 10/2005 | Arnold ............... G01R 19/16542 320/150 |
| 2006/0028172 | A1 | 2/2006 | Vaillancourt et al. |
| 2006/0043928 | A1 | 3/2006 | Nakasho et al. |
| 2006/0074405 | A1 | 4/2006 | Malackowski et al. |
| 2006/0170426 | A1 * | 8/2006 | Atehortua ........... G01R 31/3651 324/429 |
| 2007/0085496 | A1 | 4/2007 | Philipp et al. |
| 2007/0103121 | A1 | 5/2007 | Johnson et al. |
| 2007/0182369 | A1 | 8/2007 | Gerber et al. |

OTHER PUBLICATIONS

PCT App. No. PCT/US2006/040960, "ISA Search Report and Written Opinion", Oct. 2007.

PCT App. No. PCT/US2006/040960, "Partial Search Report", Jul. 2007.

Philips Semiconductor, P89LPC924/925, "Operating Manual", Dec. 2004.

"Search Report" for EP App. No. 10 014 703.2, Feb. 2011.

* cited by examiner

METHOD OF LASER WELDING THE HOUSING OF A RECHARGEABLE BATTERY

RELATIONSHIP TO EARLIER FILED APPLICATIONS

This application is a divisional of U.S. patent application Ser. No. 14/031,380 now U.S. Pat. No. 9,142,292. U.S. patent application Ser. No. 14/031,380 is a divisional of U.S. patent application Ser. No. 12/582,740 filed 21 Oct. 2009, now U.S. Pat. No. 8,564,242. U.S. patent application Ser. No. 12/582,740, is a divisional of U.S. patent application Ser. No. 11/551,335 filed 20 Oct. 2006, now abandoned. U.S. patent application Ser. No. 11/551,335 claims priority under 35 U.S.C. Sec 119 from U.S. Provisional Patent App. No. 60/729,338 filed 21 Oct. 2005. The contents of the priority applications are incorporated herein by reference.

FIELD OF THE INVENTION

This invention is related to a system and method for recharging a battery. More particularly, this invention is related to a system and method for both charging a battery and evaluating the state of health of the battery. This invention is further related to a system and method for obtaining data from the power consuming devices to which a battery is connected.

BACKGROUND OF THE INVENTION

A battery often energizes a powered surgical tool used in an operating room to perform a surgical procedure. The use of a battery eliminates the need to provide a power cord connected to an external power source. The elimination of the power cord offers several benefits over corded surgical tools. Surgical personnel using this type of tool do not have to concern themselves with either sterilizing a cord so that it can be brought into the sterile surgical field surrounding the patient or ensuring that, during surgery, an unsterilized cord is not inadvertently introduced into the surgical field. Moreover, the elimination of the cord results in the like elimination of the physical clutter and field-of-view blockage the cord otherwise brings to a surgical procedure.

In an operating room, batteries are used to power more than the tools used to perform the surgical procedure. Batteries are also used to energize the power consuming components integral with a personal protection system surgical personnel sometimes wear when performing a procedure. This system typically includes some type of hooded garment. Internal to the garment is a ventilation unit for circulating air within the garment. Some of these systems also have lights for illuminating the surgical site or radios that facilitate conventional spoken level conversation with other persons involved in performing the procedure. Each of these units, the ventilation unit, the light unit and the radio, requires a source of power. By providing this power from the battery, the need to attach cords to each individual wearing such a unit is eliminated. This, in turn, reduces number of cords in the operating room persons would otherwise have to avoid. Further, eliminating these cords likewise eliminates the restrictions of movement they place on the individual using the system.

An integral part of any battery-powered device is, naturally, the battery. Most battery-powered surgical devices used in an operating room are designed to be used with rechargeable batteries. These rechargeable batteries typically include one or more NiCd cells. Once a battery is discharged, it is coupled to a complementary charger. The charger applies a current to the battery's cells to store energy in the cells.

Unlike other rechargeable batteries, a rechargeable battery intended for use with a surgical tool must be sterilizable so that it can be placed in close proximity to the open surgical site on a patient. Often, these batteries are sterilized by placing them in an autoclave wherein the atmosphere is saturated with water vapor (steam), the temperature is approximately 270° F. (132° C.) and the atmospheric pressure is approximately 30 psi (Gage) (1552 mmHg). The repetitive exposure to this environment causes a battery cells' ability to store electric charge to degrade. Often this is referred to as degradation in the "state of health" of the battery.

The Applicant's U.S. Pat. No. 6,018,227, BATTERY CHARGER ESPECIALLY USEFUL WITH STERILIZABLE RECHARGEABLE BATTERY PACKS, issued Jan. 25, 2000 and incorporated herein by reference, discloses a means to determine the voltage at load of a battery. Inferentially, this is a measure of the internal resistance of the battery. Unfortunately, this information alone does not provide a complete measure of the battery state of health. For example, this information alone does not provide information if the stored energy is sufficient to power the device to which the battery is attached for the time required to perform the surgical procedure. This means that, during the performance of a procedure, if the battery's stored energy appreciably depletes, the procedure is interrupted to replace the battery. This increases the overall time takes to perform the procedure. This interruption runs contrary to one of the goals of modern surgery which is to perform the procedure as quickly as possible so as to lessen the time the patient's internal organs are exposed, and therefore open to infection, and the amount of time a patient is held under anesthesia.

Moreover, there is an interest in having surgical equipment provide data regarding their own operating states to other equipment in the hospital. For example, some motorized surgical tools are provided with internal temperature sensors. In the event a bearing assembly internal to a tool of this type malfunctions, tool temperature will start to rise. This rise in temperature is detected by the complementary sensor. The output signal from the sensor can then be read by a remote device in the hospital. This gives hospital personnel notice that the tool may be approaching a critical malfunction and should be repaired or replaced.

Corded surgical devices provide these types of operating state data. These communications systems are relatively simple technically and economical to provide because the signals are forwarded to the complementary control consoles through the cords through which power is supplied to these devices. One can also provide the data from these devices through wireless communications systems. One system is disclosed in the Applicant's U.S. Patent Application No. 60/694,592, POWERED SURGICAL TOOL WITH SEALED CONTROL MODULE, filed 28 Jun. 2005, the contents of which are published in U.S. Pat. No. 7,638,958 B2, incorporated herein by reference. A disadvantage of the above-mentioned system is that it requires the addition of a wireless communications system into the operating room. The expense of providing such a system limits the locations where they are installed.

The Applicant's Assignee's U.S. Pat. No. 5,977,746, RECHARGEABLE BATTERY PACK AND METHOD FOR MANUFACTURING SAME, issued 2 Nov. 1999 and incorporated herein by reference, discloses a rechargeable battery especially designed to withstand the rigors of autoclave sterilization. The battery of this invention includes a cluster of cells that are bound together by top and bottom plastic binders. Conductive straps extending between openings formed in the binders connect the cells. One of the straps is a fuse that opens upon a more than a specific current flowing through it. More specifically, the current through the fuse heats the material forming the fuse so a section of the fuse vaporizes. This vaporization of the fuse section separates the rest of the fuse into two sections.

The above battery pack has proven useful for storing the charge needed to energize a cordless surgical tool. However, the cells internal to the battery pack can generate significant amounts of heat. This causes the temperature of the cells to rise. Sometimes, the temperature rise between the cells is uneven. This uneven thermal loading of cells can result in an electrical imbalance of the cells. If the cells become so imbalanced, both the immediate utility of the battery to supply energy at a particular time and its useful lifetime may diminish.

SUMMARY OF THE INVENTION

This invention relates to a new and useful battery and battery charging system. The battery is designed for use in a harsh environment such as in a hospital where the battery is autoclave sterilized. The battery and battery charging system of this invention are further designed to record and transmit data about the devices the battery is used to energize.

The battery of this invention includes a set of rechargeable cells. Also internal to the battery are a data recording unit and a temperature sensor. Both the data recording unit and temperature sensor are powered by the battery cells so that they are always on, regardless of whether or not the battery is being used to power a device or is being charged. Collectively, the data recording unit and temperature sensor are configured to record data about the temperature of the battery.

The battery charger of this invention includes a current source for charging the battery. Also internal to the battery charger is a processor and a load resistor. The processor regulates the actuation of the current source and connection of the battery to the load resistor.

The processor also reads the data stored in the battery data recording unit. Depending on the data indicating the history of the battery, the processor may conduct a state of health evaluation of the battery. For example, a state of health evaluation may be performed if the data in the data recording unit indicates that battery was continually at a temperature above a threshold level for more than a given period of time. To perform a state of health evaluation, the processor both measures the voltage-at-load of the battery and the quantity of energy input to the battery. Often, this last evaluation is made by first fully discharging the battery. The results of the state of health evaluation are displayed.

Another feature of this invention is that, while the battery is being used to power a device, the device writes data into the data recording unit. When the battery is attached to the charger, the data recording unit writes out the stored device data to the charger processor. The charger processor, in turn, forwards these data to another device. Thus, information about the operating state of a battery powered device is available to persons charged with maintaining the device. This information is available even though there is no corded link or RF/IR/ultrasonic wireless communications link to the device.

The battery of this invention is also configured to foster uniform dissipation of the heat generated by the cells internal to the pack. This minimizes the temperature imbalance of the cells. The minimization of the temperature imbalance reduces the electric imbalance between the cells. The reduction of this electrical imbalance results in a like reduction in the extent to which the cells, if electrically imbalanced, adversely affect battery performance. The battery of this invention is further constructed to have a fuse that will regularly open when a defined amount of current flows through the fuse. The battery of this invention is also economical to manufacture and occupies a relatively small surface area.

BRIEF DESCRIPTION OF THE DRAWINGS

The invention is pointed out with particularity the in the claims. The above and further features and benefits of the battery, battery charger and method for charging a battery of this invention may be better understood from the following detailed description taken in conjunction with the accompanying drawings in which:

DETAILED DESCRIPTION

I. Overview

Figure 1:
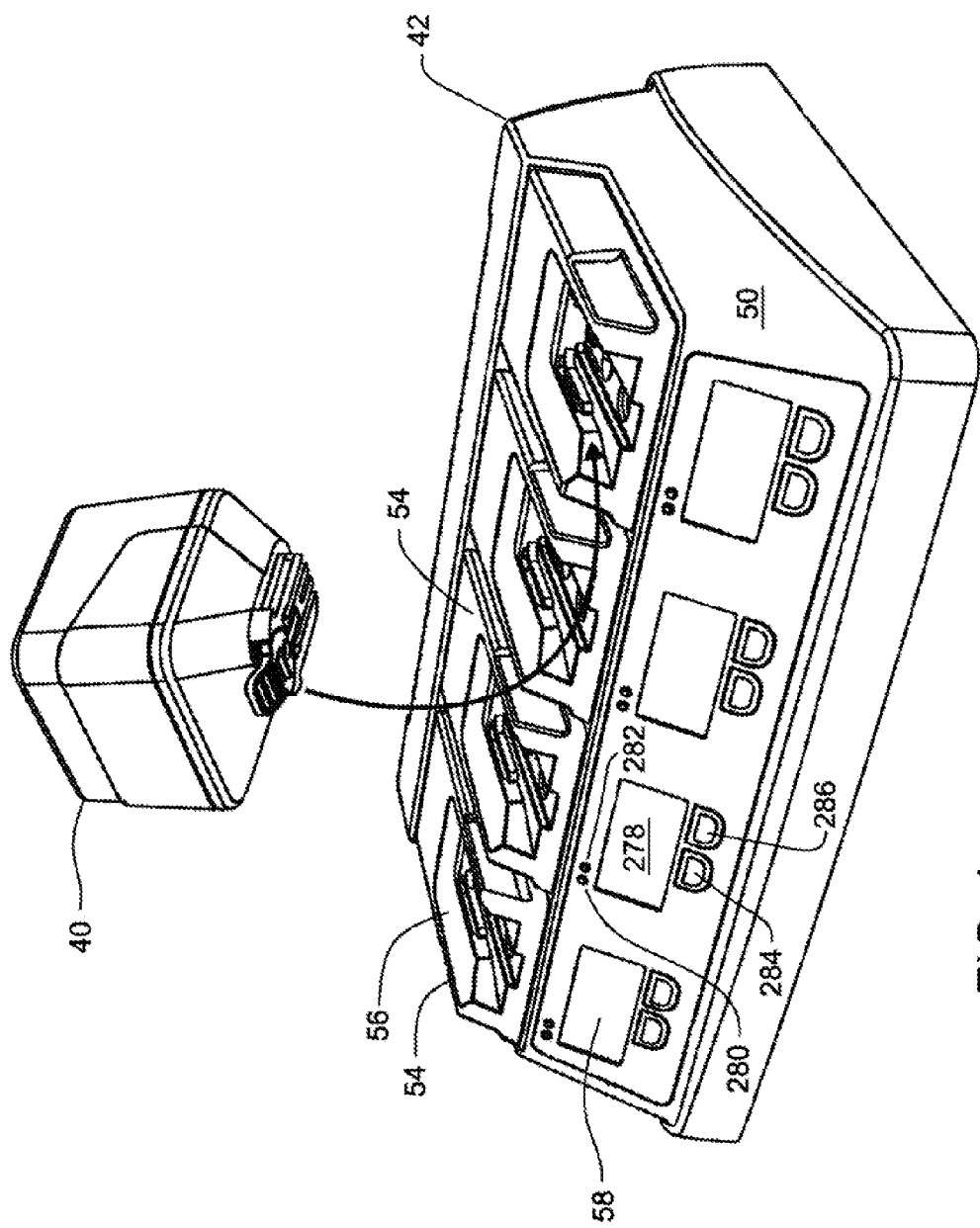
FIG. 1 is a perspective view of a battery and battery charger of this invention.
Figure 12:
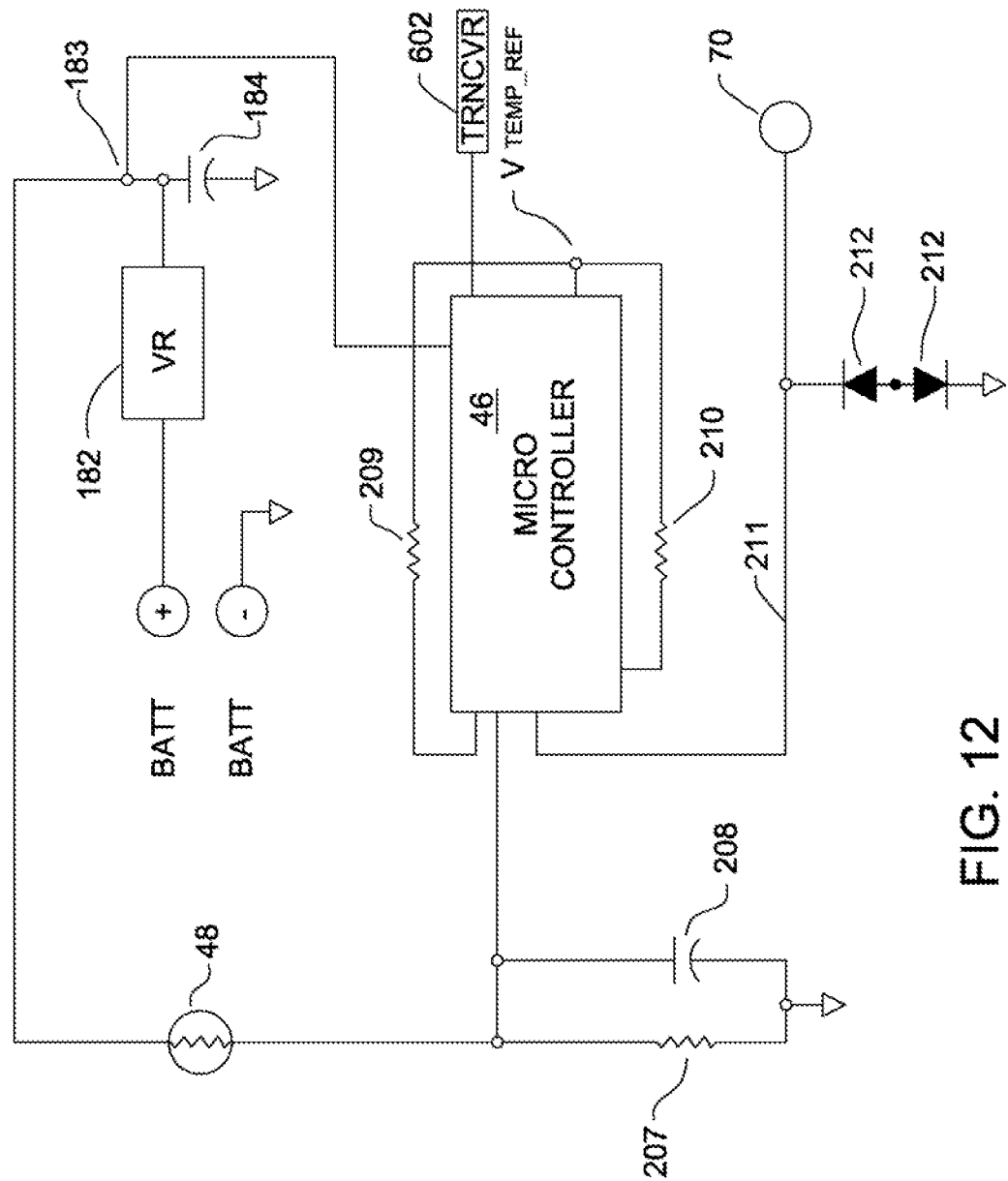
FIG. 12 is a schematic drawing of the electrical components internal to the battery.
Figure 20:
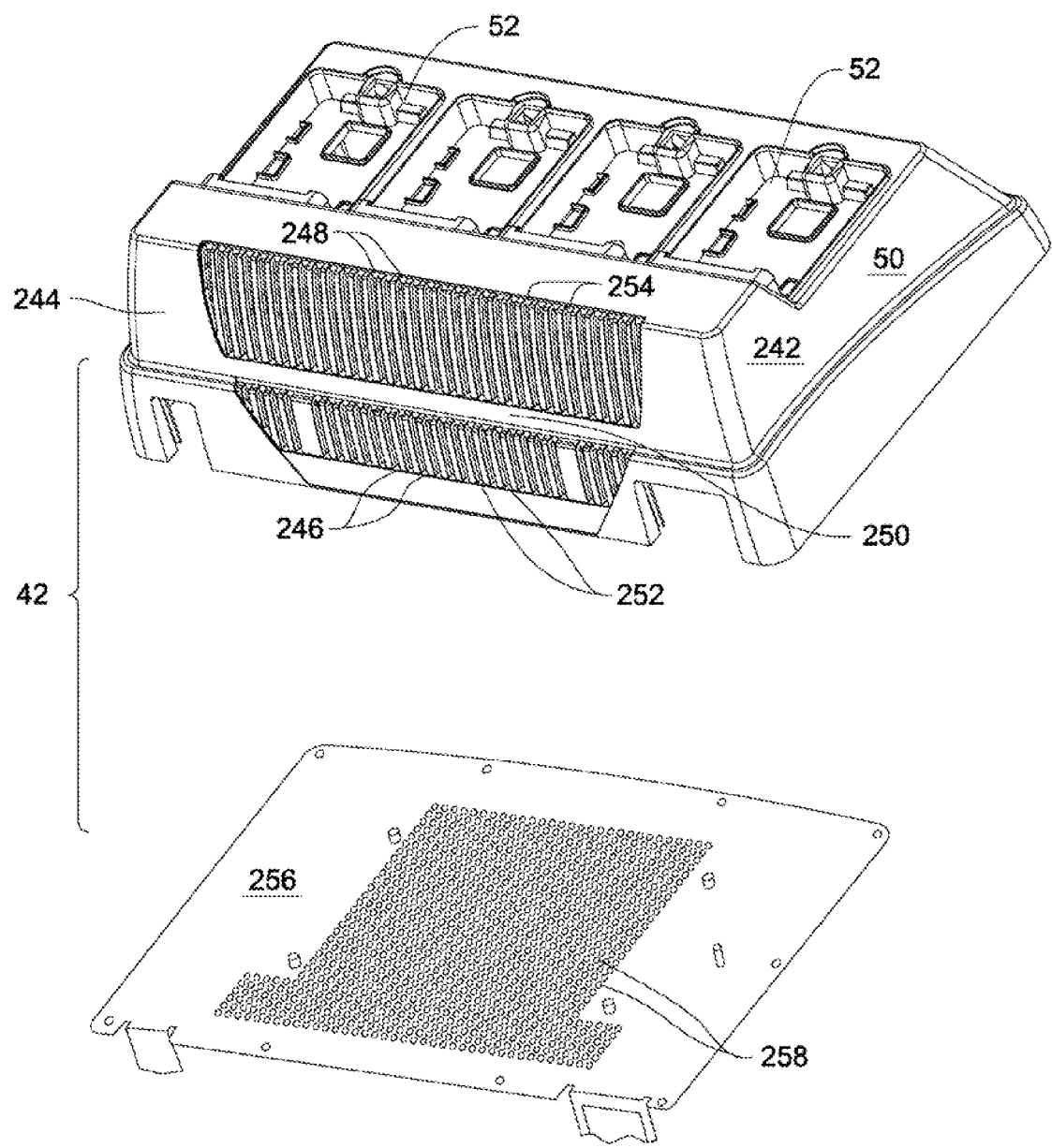
FIG. 20 is an exploded view of relationship of the charger base to the charger housing.

FIG. 1 illustrates a battery 40 and battery charger 42 constructed in accordance with this invention. Battery 40, includes a set of rechargeable cells 44 (FIG. 3) a microcontroller 46 and a temperature sensor 48 (FIG. 12). Battery charger 42 includes a housing 50 with a number of pockets 52 (FIG. 20). Each pocket 52 removably receives a module 54 associated with a specific type of battery. The module 54 is shaped to define a complementary socket 56 for receiving the head end of the associated battery 40. Internal to the battery charger 42 are components for reading the data stored in the battery microcontroller 46 and for charging the battery cells 44. A plurality of I/O units 58 are attached to the charger 42. Each I/O unit 58 functions as the sub-assembly through which instructions are entered and charge state information presented about an individual one of the batteries 40 attached to the charger 42.

II. Battery and Method of Battery Assembly

Figure 2:
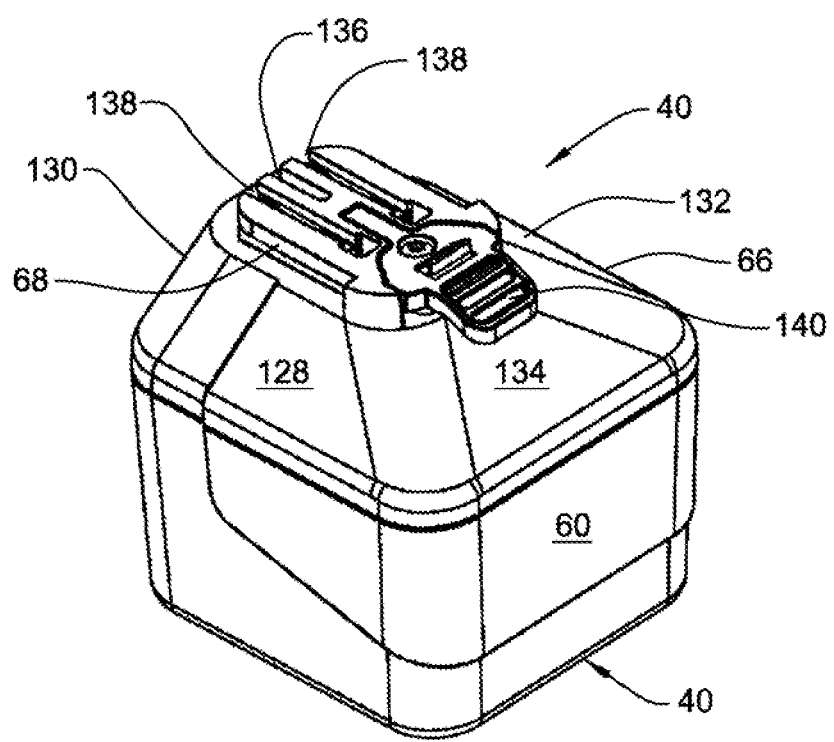
FIG. 2 is a perspective view of the battery.
Figure 3:
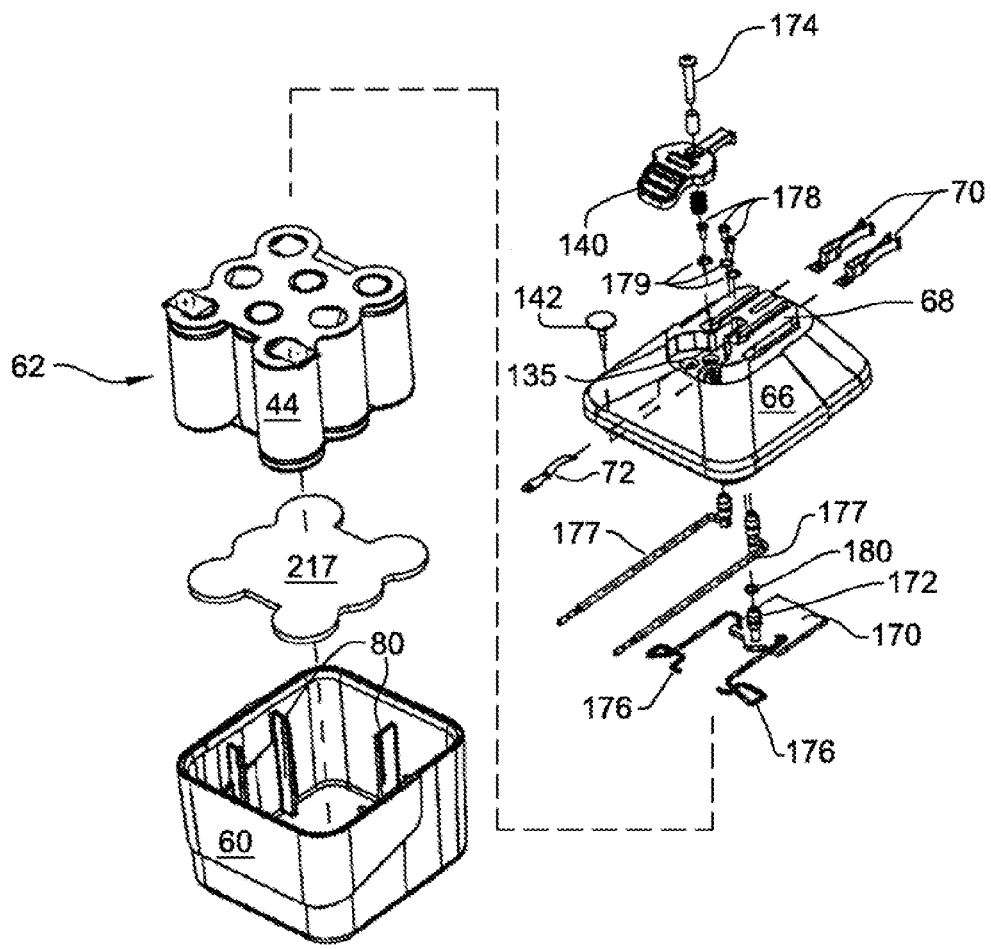
FIG. 3 is an exploded view of the battery of this invention.

As seen in FIGS. 2 and 3, a battery 40 of this invention includes a housing 60. Rechargeable cells 44 are arranged in a cluster 62 seating in housing 60. A lid 66 is sealing disposed over the open top end of the housing 60. Lid 66 is formed with a head 68. The lid 66 is the battery structural component to which the microcontroller 46 and temperature sensor 48 are mounted. In the illustrated version of the invention, the lid head 68 is dimensioned to fit into a complementary socket formed in the power tool 522 (FIG. 22) the battery 40 is intended to power. The lid head 68 is provided with two contacts 70 and a single contact 72. Contacts 70 are the conductive members through which the charger 42 applies a charging current to the cells 44 and from which the power tool 522 (FIG. 23) draws an energizing current. Contact 72 is the contact through which data and instructions are written into and read out from the microcontroller 46. Thus, data are exchanged between the charger 42 and battery microcontroller 46 using a one-wire signal exchange protocol. One such protocol is the Dallas Semiconductor One-Wire protocol.

Battery housing 60 is formed from a single piece of plastic that is transmissive to light energy emitted at 980 nanometers. By "transmissive" it is understood the plastic is at least "partially" transmissive. In most versions of the invention the plastic is at least 55% percent transmissive. In more preferred versions, the plastic is at least 75% transmissive. In one version of the invention, housing 60 is formed from a polyphenylsulfone plastic. One such plastic from which housing 60 is formed is sold under the brand name RADEL by Solvay Advanced Polymers, of Alpharetta, Ga., United States. This plastic is partially transparent. For aesthetic reasons, the plastic forming housing 60 may be dyed to be opaque at visible wavelengths. If housing 60 is so dyed, the dye should be selected so that it does not appreciably interfere with transmissivity of photonic energy at the 980 nanometer range. As discussed below this is the wavelength at which, in one process lid 66 is laser welded to housing 60.

Figure 4:
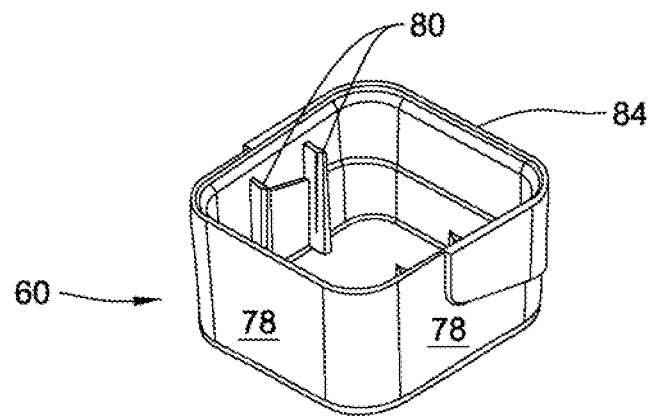
FIG. 4 is a perspective view of the battery housing.
Figure 5:
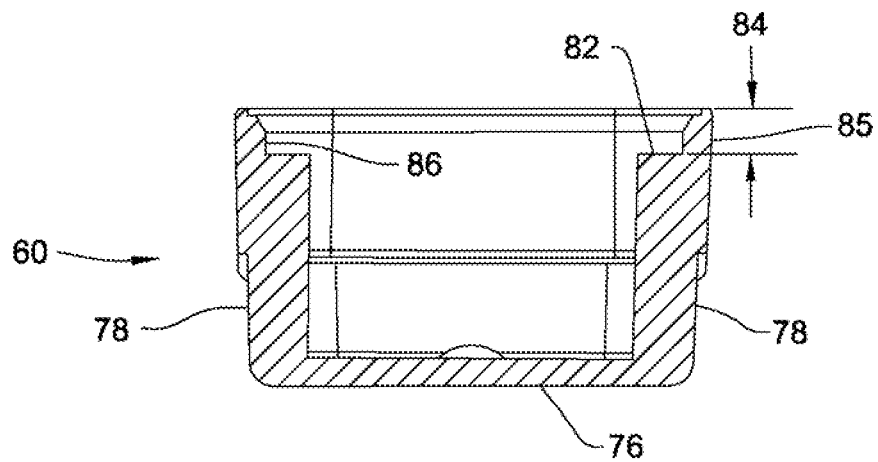
FIG. 5 is a cross sectional view of the battery housing.
Figure 5A:
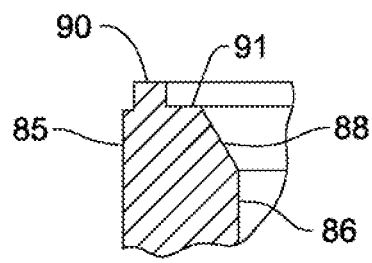
FIG. 5A is an enlarged cross sectional view of the top edge of the battery housing.

As seen in FIGS. 4, 5 and 5A, housing 60 is formed to have a generally rectangular base 76. Four interconnected walls 78 extend upwardly from the perimeter edges of the base 76. For aesthetic reasons, the corners of the base 76 and the corners where walls 78 abut are rounded. Housing 60 is further shaped so that walls 78 taper outwardly away from base 76. The housing 60 is further formed so that ribs 80 extend inwardly from the inner surfaces of the walls 78 from the top surface of the base 76. Each wall 78 may be formed with one, two or more ribs 80. Ribs 80 provide structural rigidity to the walls and minimize movement of the cell cluster 62 within the housing 60.

Each housing wall 78 has an inner vertical surface 86. (In the cross sectional view of FIG. 5 rib 50 is seen below the top of the inner surface 86.) Above the inner vertical surface 86 there is a tapered face 88 that angled outwardly relative to the vertical surface 86. A reveal 90 forms the top most portion of each lip 78. The reveal 90 has a generally square cross sectional profile. The width of the reveal 90 is less than that of the vertical surface 91 that extends between the top edge of the lip outer surface 85 and the top edge of tapered inner face 88. Housing 60 is thus formed so that reveal 90 is located inwardly of both the top edge of the lip outer surface and the top edge of the tapered inner face 88.

Figure 6:
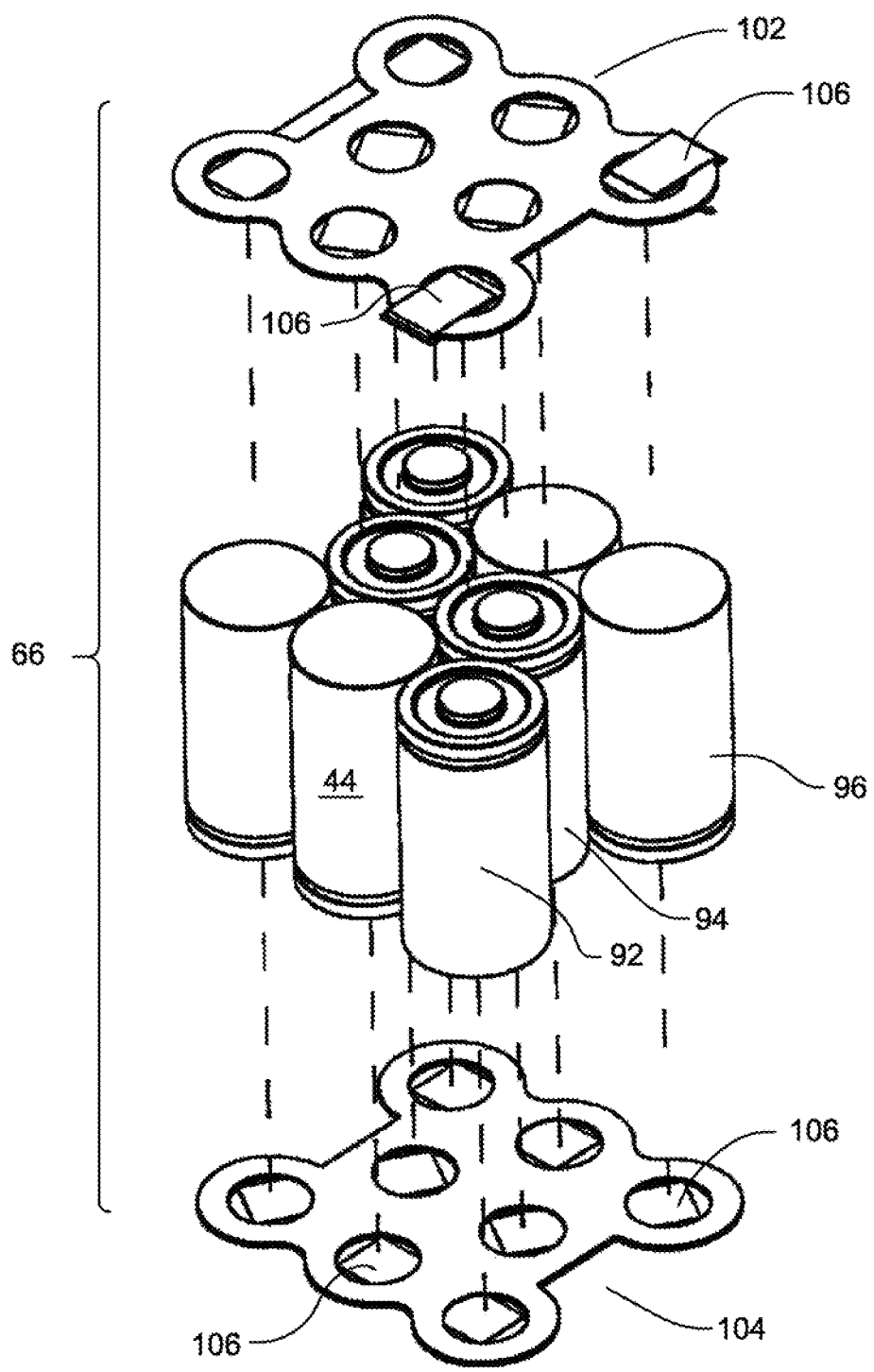
FIG. 6 is an exploded view of the cell cluster internal to the battery.

As seen by reference to FIG. 6, the cell cluster 62 includes a plurality of rechargeable cells 44. As is known from the above-identified, incorporated herein by reference U.S. Pat. No. 5,977,746, the outer cylindrical surface of each cell 44, which functions as the cell ground, is covered with polyimide tape, (not shown).

Cells 44 are arranged in a three abutting rows 92, 94 and 96, such that the cells in one row abut the cells in the adjacent row. In each row 92-94, the adjacent cells 44 abut. The cells 44 are arranged so that there are three cells in the outer rows, rows 92 and 96, and two cells in the center row, row 94. This arrangement ensures that each cell has an outer perimeter section of at least 10% and, more preferably at least 20%, that neither abuts an adjacent cell nor is concealed behind an adjacent row of cells. Thus a perimeter section of at least 10%, and more preferably at least 20%, of each cell 44 forms a portion of the outer perimeter of the array of cells forming the cell cluster 62.

The top and bottom orientation, the orientations of, respectively, the positive and negative terminals, of the cells 44 is arranged as a function to the extent the cells are to be connected together in a series or parallel arrangement in order to provide a charge at a particular voltage level and current.

Figure 7:
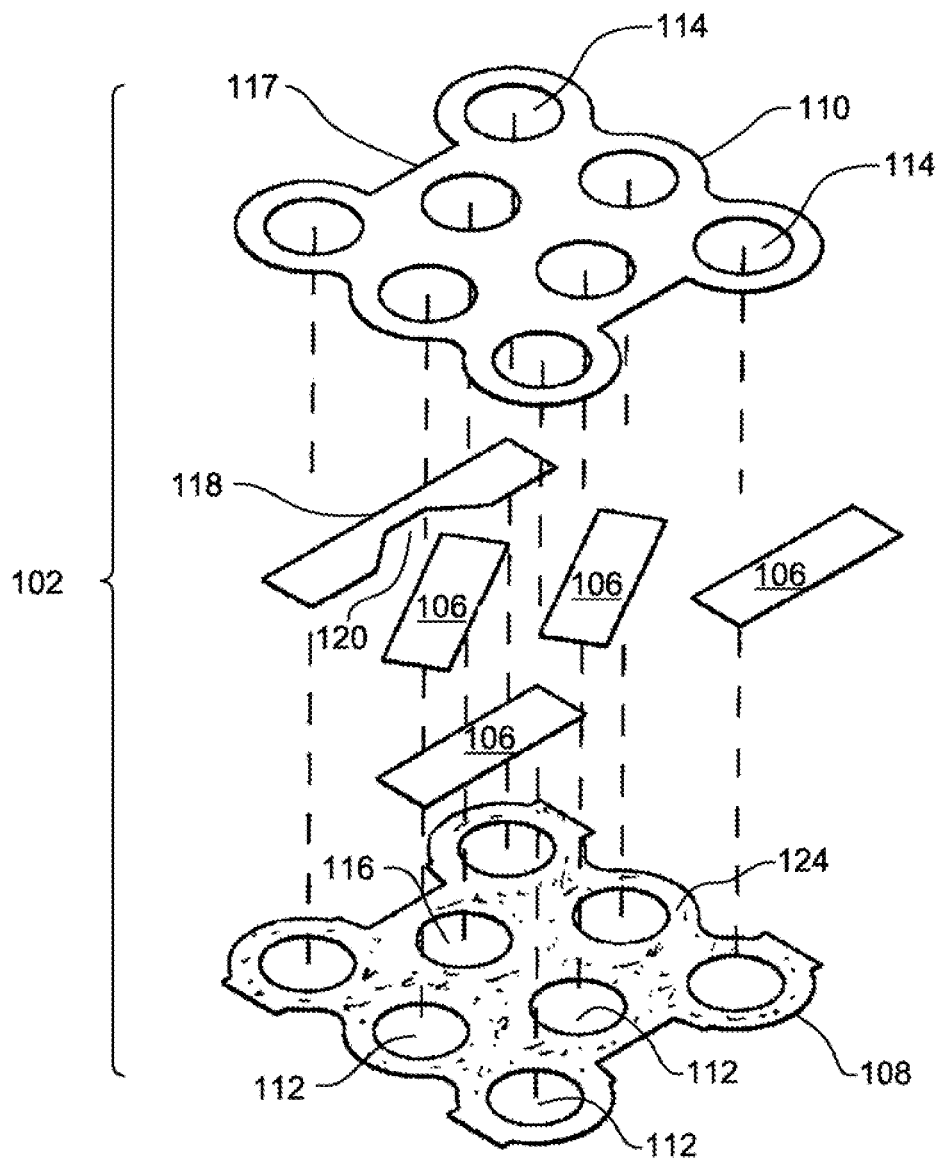
FIG. 7 is an exploded view of the binder assembly, here the top binder assembly, of the cell cluster.

The cells 44 are held together to form the cluster 62 by top and bottom binder assemblies 102 and 104, respectively. Each binder assembly 102 and 104 includes a number of conductive straps 106 that are in the form of thin strips of metal. As seen in FIG. 7, which shows the top binder assembly 102, each binder assembly includes inner and outer binders 108 and 110, respectively. (For reference, the "inner" binder is understood to be the binder closest to the cells 44; the "outer" binder is spaced from the cells.) Each binder 108 and 110 is formed from a flexible plastic material such as a polyester sold under the trademark MYLAR by DuPont. Each binder 108 and 110 is formed with a number of openings 112 and 114, respectively. Binders 108 and 110 forming the upper binder assembly 102 are further formed so as to define along the outer perimeter thereof aligned notches 116 and 117, respectively.

Conductive straps 106 are sandwiched between the binders 108 and 110. Each conductive strap 106 is positioned to have one end that extends into the space subtended by aligned pair of binder openings 112 and 114. Some conductive straps 106 are positioned so that that the second ends of the straps extend into one of the aligned pairs of binder openings 112 and 114. These conductive straps 106 electrically connect the terminals of adjacent cells 44. Two of the conductive straps 106 are positioned so that their second ends project beyond the perimeters of the binders 108 and 110. These two conductive straps 106, seen in FIG. 6, function as the members that provide electrical connections between the cell cluster 62 and the contacts 70.

Figure 8:
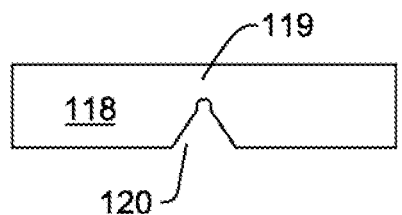
FIG. 8 is a plan view of the thermal fuse internal to the top binder assembly.

A fuse 118 is also disposed between the binders 108 and 110 forming top binder assembly 102. The fuse 118, best seen in FIG. 8, is formed of a conductive metal that when the current flow therethrough causes material heating to the point the metal vaporizes. In one version of the invention, fuse 118 is formed from nickel or a nickel alloy. Fuse 118 is generally in the form of a planar strip. The fuse 118 is further formed so as have notch 120 that extends inwardly from the one of the longitudinal side edges of the metal strip forming the fuse. (The geometries of notch 120 of the fuse of FIG. 7 and of the fuse 118 of FIG. 8 are slightly different.) In FIG. 8, section 119 of fuse 118, the narrowest width section, defines the widest portion of notch 120.

A binder assembly 102 or 104 of this invention is assembled by first placing one of the binders 108 and 110 in a jig. More particularly, the jig is formed with a recess designed in which the binders 108 and 110 are designed to precisely seat. Extending into the recess from the base of the jig are spaced apart fingers. The fingers extend through into the spaces subtended by binder openings 112 and 114. The fingers are spaced so as to define spaces therebetween into which the conductive straps 106 and fuse 118 are seated.

The exposed surface of the binder 108 or 110 seated in the jig recess is provided with an adhesive. In some versions of the invention, the adhesive is pre-applied to the binder 108 or 110. At manufacture, a protective sheet that covers the adhesive is removed. In FIG. 7, the adhesive is represented as stippling 124 on inner binder 108.

Once the first binder 108 or 110 is set in the jig, the conductive straps 106 and fuse 118 are set over the binder. More specifically, the conductive straps 106 and fuse 118 are set between the fingers that extend through the binder openings 112 or 114. The second binder 110 or 108 is then disposed over the partially assembled unit. In some versions of the invention, adhesive material may also disposed over the surface of the second binder that abuts the first binder.

As a consequence of the assembly of the binders 108 and 110, each inner binder opening 112 is aligned with an associated one of the upper binder openings 114. Inner and outer binder notches 116 and 117, respectively, are also aligned. It should further be appreciated that, during the assembly of the binder assembly 102, fuse 118 is positioned so that fuse notch 120 is within the area where the binders 108 and 110 are sandwiched together. The portion of the fuse 118 that defines fuse notch 120 is within the space subtended by binder notches 116 and 117. In more preferred versions of the invention, the fuse is positioned so that the thinnest section of the fuse, the portion defining the widest section of fuse notch 120, is spaced from the binders 108 and 110.

Figure 9:
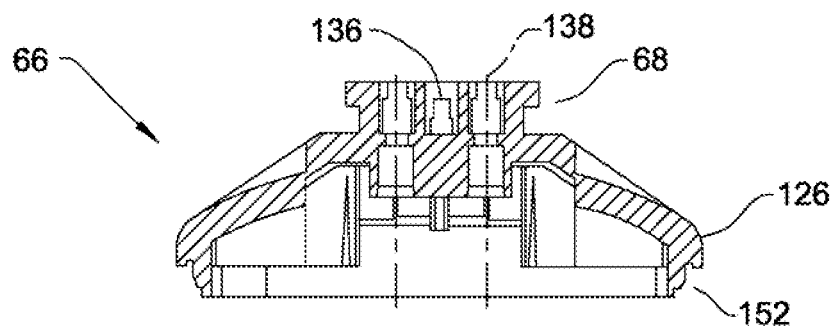
FIG. 9 is a cross sectional view of the battery lid.
Figure 10:
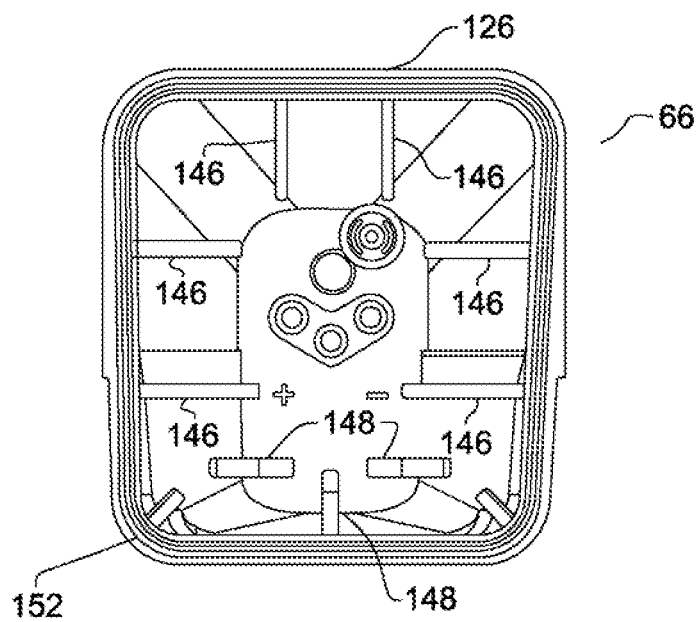
FIG. 10 is a plan view of the undersurface of the battery lid.

The battery lid 66 is now described by reference to FIGS. 2, 9, and 10. In one version of the invention, lid 66 is a single component formed from a polyphenelsulfone plastic such as the RADEL R plastic. For aesthetic reasons, the plastic forming the lid may be dyed to be opaque at the visible wavelengths. If the lid 66 is to be secured to the housing 60 by the below discussed laser welding process, the lid should be formed of material that absorbs the photonic energy at the wavelength emitted by the laser. The aesthetic dye can function as this material. Thus, in the described version of the invention, the dye absorbs energy emitted in the 980 nanometer range. Lid 66 is shaped to have a generally rectangular base 126 that has a geometry that subtends the top edges of the housing walls 78. Four panels 128, 130, 132 and 134 extend inwardly and upwardly from the sides of the base 126. The panels 128-134 meet at a planar horizontal surface 136 from which the battery head 68 upwardly projects. Panels 128 and 132 are the side panels and are symmetric relative to each other. Panel 130 is the front panel; panel 134 is the rear panel. Relative to the horizontal plane, front panel 130 has a steep upward slope; the slope of rear panel 134 is shallower.

Battery head 68 is formed to have a slot 136 and two slots 138. Each of slots 136 and 138 are open to the front face of the head 68. Slot 136 is centered along the longitudinal centerline of the battery 40. Slots 138 are parallel to and located on either side of slot 138. Contact 72, the contact through which signals are exchanged with microcontroller 46 extends into slot 136. Contacts 70, the contacts through which charge is stored in and drawn from cells 44, is disposed in slots 138.

A latch 140 is pivotally mounted to the battery head. The latch 140 holds the battery 40 to the power consuming device to which the battery is connected. A pressure relief valve 142 is mounted to horizontal surface under the latch 140. Not identified are the openings in which latch 140 and valve 142 are mounted and the assembly that pivotally holds the latch to the battery lid 66.

A number of ribs 146 and 148 extend inwardly from the inner surface of lid panels 128-134. The ribs 146 and 148 are generally rectangular in shape and extend into the inner surface of the lid below horizontal surface 135. Ribs 146 are relatively tall; ribs 148 are short. Two ribs 146 extend inwardly from panels 128, 132 and 134. A single rib 148 extends inwardly from front panel 130. An additional rib 148 extends inwardly from each of the side panels 128 and 132 immediately adjacent the front panel. Each rib 148 is further formed so that the outer end is downwardly stepped relative to the portion of the rib immediately adjacent the panel from which the rib extends. Ribs 146 and 148 minimize, if not completely block, vertical displacement of the cell cluster 62.

Figure 11:
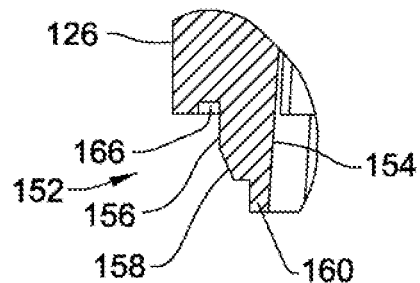
FIG. 11 is an enlarged cross sectional view of the bottom lip of the battery lid.

Battery lid 66 also has a lip 152 that extends downwardly from the base 126 around the perimeter of the lid. As seen best in FIG. 11, the lip 152 is located inwardly of the outer vertical surface of the base 126. Lid 66 is formed so that lip 152 has an inner vertical surface 154 that is flush with the adjacent inner surface of the base 126. The lip 152 has an outer vertical surface 156 located inward of the outer perimeter of the base 126. The lip 152 is further formed to have a tapered surface 158 that extends below vertical surface 154. Surface 158 tapers inward toward the center of the lid 66. A rectangularly shaped flange 160 forms the bottommost portion of lip 152 and, by extension, the bottommost structural feature of the battery lid 66. The bottommost portion of inner vertical surface 154 forms the inner surface of flange 160. A parallel vertical surface 164 that is inwardly stepped relative to the adjacent surface 158 forms the outer wall of the flange 160.

Battery lid 66 is further formed to define a rectangular notch 166 that extends upwardly from the bottom surface of base 126. The base 126 is formed so that notch 166 is located immediately in front of and is partially defined by lip outer vertical surface 156. In some versions of the invention, the notch is absent from the lid 66.

Returning to FIG. 3, it can be seen that a printed circuit board 170 is mounted in the battery lid 66. Printed circuit board 170 is the component to which battery microcontroller 46 and temperature sensor 48 are mounted (not illustrated). Circuit board 170 is fitted in the lid 66 to seat against the inwardly stepped edges of ribs 148. A post 172 extends upwardly from the printed circuit board 170. A screw 174 that extends through lid horizontal surface 135 into post 172 holds the circuit board 170 to the lid.

Seen extending from circuit board 170 are two conductors 176. Conductors 176 provide an electrical connection between the cells 44 and the components on the circuit board 170. As discussed in more detail below, energization signals are continually applied to microcontroller 46 and temperature sensor 48 of battery 40 regardless of whether or not the battery is being charged, discharged, autoclaved, or simply in storage.

Also seen in FIG. 3 are the wire assemblies 177 that extend from the cell cluster to contacts 70. Also seen in the Figure but not otherwise described further are the button head fasteners 178 and lock washers 179 that hold the contacts 70 and 72 in position. Also seen is the O-ring 180 disposed around post 172.

FIG. 12 is a schematic of the electrical circuit components integral with the battery 40. A voltage regulator 182 is connected to the positive output terminal of the cell cluster 62. In one version of the invention voltage regulator produces a 3.3 VDC signal, the signal present at point 183. A capacitor 184, tied between the pin of the voltage converter 182 at which the 3.3 VDC signal is present and ground, filters the 3.3 VDC signal.

One of the components to which the 3.3 VDC signal is applied is the microcontroller 46. One suitable unit that can be used as microcontroller 46 is the P89LPC925 8 bit microcontroller manufactured by Philips Electronics N.V. of the Netherlands. Microcontroller 46 has a number of different sub-circuits, a number of which are now described by reference to FIG. 13. A central processing unit (CPU) 185 controls most of the operation of microcontroller 46 and the components connected to the microcontroller. A non volatile flash memory 187 stores instructions executed by the CPU 185. As discussed below, memory 187 also stores: the instructions used to regulate the charging of the battery; data describing the use history of the battery; and data describing the use history of the tool 522 to which the battery is attached.

A random access memory 188 functions as a temporary buffer for data read and generated by microcontroller 46. A CPU clock 189 supplies the clock signal used to regulate the operation of the CPU 185. While shown as single block for purposes of simplicity, it should be appreciated that CPU clock 189 includes an on-chip oscillator as well as sub-circuits that convert the output signal from the oscillator into a CPU clock signal. A real time clock 190 generates a clock signal at fixed intervals as discussed below.

Figures 13, 14:
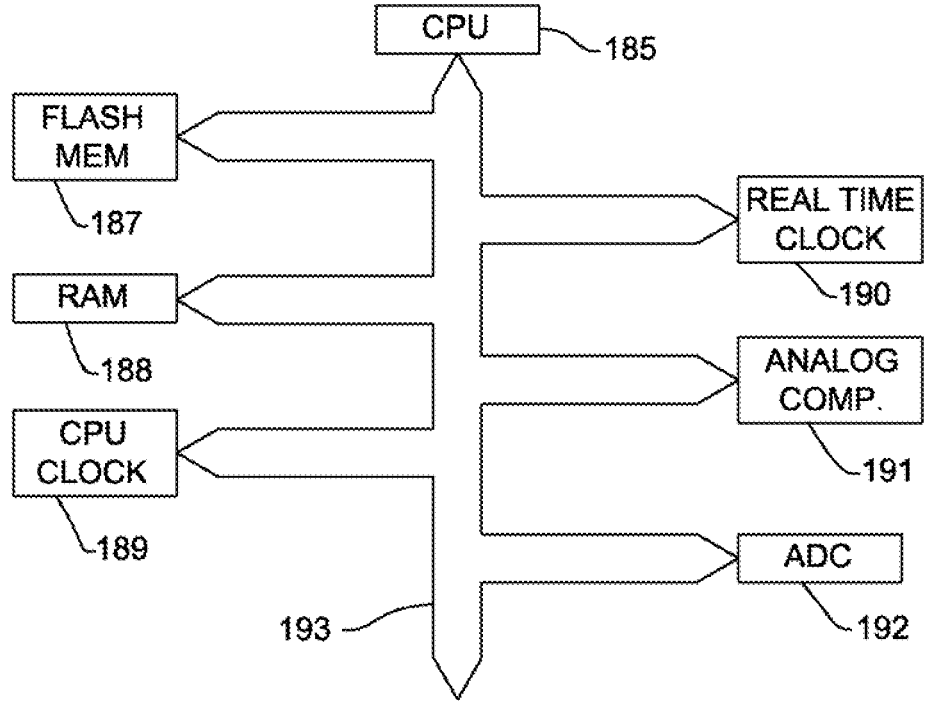
FIG. 13 is a block diagram of some of the sub circuits internal to the battery microcontroller.
FIG. 14 depicts some to types of data stored in the memory integral with the battery microcontroller.

The output signal from the temperature sensor is applied to both an analog comparator 191 and an analog to digital converter 192. In FIG. 13 the above sub-circuits are shown interconnected by a single bus 193. It should be appreciated that this is for simplicity. In practice, dedicated lines may connect certain of the sub circuits together. Likewise it should be understood microcontroller 46 may have other sub-circuits. These sub-circuits are not specifically relevant to this invention and so are not described in detailed.

FIG. 14 illustrates types of data stored in the flash memory 187 in addition to the instructions executed by the microcontroller 46. These data include, in a field or file 194, data that identifies the battery. These data, in addition to serial number, lot number and manufacturer identification can include data such as an authorization code. This code is read by the tool 522 or charger 42 to which the battery is connected to determine if, respectively the battery can power the tool or be recharged by the charger. The battery identification data may include data indicating the useful life of the battery. Useful life data are understood to be one or more of the following data types: battery expiration data; number of chargings; and number of autoclavings. Other data in identification file 194 can indicate the nominal open circuit voltage of the signal produced by the battery, the current the battery can produce and the joules of available energy.

Charging instructions for the battery are stored in a file 195. These data can be the types of data described in the memories of the batteries disclosed in incorporated by reference U.S. Pat. Nos. 6,018,227, and 6,184,655. Flash memory 187 also contains data describing the charging and autoclave histories of the battery. In a field 196 data are stored indicating the number of times the battery was charged. A measured post-charge voltages file 197 contains data indicating the measured voltages-at-load of the battery after each charging. In some versions of the invention file 197 only contains these measurements for the last 1 to 10 chargings. In a file 198 data are stored indicating the highest battery temperature measured during its previous chargings. Again, file 198 may only contain data indicating the highest temperatures measured during the last 1 to 10 chargings of the battery.

A field 199 stores data indicating the total number of times the battery has been autoclaved. A cumulative autoclave time field 200, as its name implies, is used to store data indicating the total time the battery has been at temperatures at or above a threshold considered to be the autoclave temperature.

A field 201 contains data indicating the number of times the battery has been exposed to potentially excessive autoclavings. Data indicating the cumulative time the battery may have been potentially excessively autoclaved is stored in a field 202. A peak autoclave temperature field 203 contains data indicating the highest autoclave temperature to which has been exposed. A file 204 contains records of the time the battery has been in the autoclave for each of its autoclavings. In some versions of the invention, time in autoclave file 204 only contains data indicating the time the battery was in the autoclave for each of its last 5 to 100 autoclavings. A file 205 contains data indicating the peak temperatures of the battery that measured during its last 5 to 100 autoclavings. In most versions of the invention, memory 187 stores autoclave time and temperature data for the exact same number of autoclavings. Field 206 contains data indicating the period of the longest single time the battery was subjected to autoclaving.

Memory 187 also contains a tool history file 229. As discussed below, tool history file 229 stores data obtained from the tool 522 that battery 40 is employed to power.

Returning to FIG. 12, other circuit components internal to battery 40 are now described. Temperature sensor 48 is any suitable temperature sensing device capable of detecting whether or not battery 40 is exposed to autoclave temperatures. In the described versions of the invention, temperature sensor 48 is a thermistor. The 3.3 VDC is applied to one end of the temperature sensor. The opposed end of the temperature sensor 48 is tied to ground through a resistor 207. A capacitor 208 is tied across resistor 207. The voltage present at the junction of the temperature sensor 48 and resistor 207 is applied as the T_SENSE signal representative of detected temperature to the noninverting input of microcontroller comparator 191 (connection not specifically shown.)

A reference voltage, $V_{TEMP\_REF}$, is applied to the inverting input of comparator 191 (connection not specifically shown.) The reference voltage is the signal present at the junction of series connected resistors 209 and 210. The opposed end of resistor 209 receives a reference voltage from a source internal to microcontroller 46. The opposed end of resistor 210 is selectively tied to ground through a switch internal to the microcontroller 46 (switch not illustrated).

Microcontroller 48 is connected to battery contact 72 by a conductor 211. A pair of series-connected opposed diodes 212 extend between conductor 211 and ground.

Figure 15A:
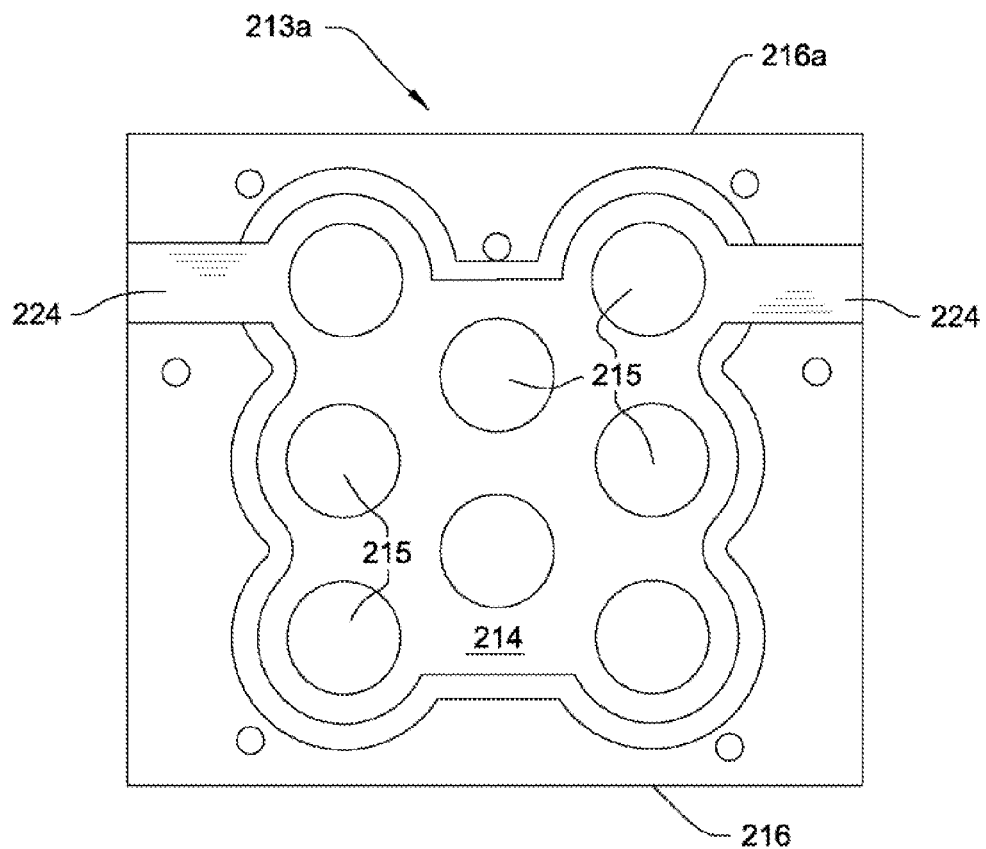
FIG. 15A is a plan view illustrating one of the fixtures in which the components forming the cell cluster are placed in order to facilitate assembly of the cluster.

As part of the process of assembling battery 40, cell cluster 62 is assembled. Initially, binder assemblies 102 and 104 are fabricated as described above. Then, a first binder assembly 102 or 104 is placed in a fixture 213a or 213b, FIG. 15A illustrating fixture 213a, the fixture in which the top binder assembly 102 is seated. Each Fixture 213a and 213b includes a base plate 214 formed with a number of openings 215. A block 216 extends upwardly from the fixture base plate. Block 216 is shaped to define a recess 223 dimensioned to slip fit receive the binder assembly 102 or 104 and cells 44. The block 216 is formed to define the pattern of the rows 92, 94 and 96 in which the cells are to be placed. Illustrated fixture 213a is further shaped to define two opposed slots 224 that are contiguous with recess 223. Slots 224 receive the free end of the top binder assembly conductive straps 106 that function as electrical connections. Thus, fixture 213a has a supplemental block 216a spaced from block 216 so as to define slots 224 therebetween.

Fixture openings 215 are formed in the fixture base plate 214 to be concentric with the binder openings 112 and 114. When a cell is fitted in the fixture 213a or 213b it should be appreciated the cell is centered with binder openings 112 and 114 and the associated fixture opening 215.

Figure 15B:
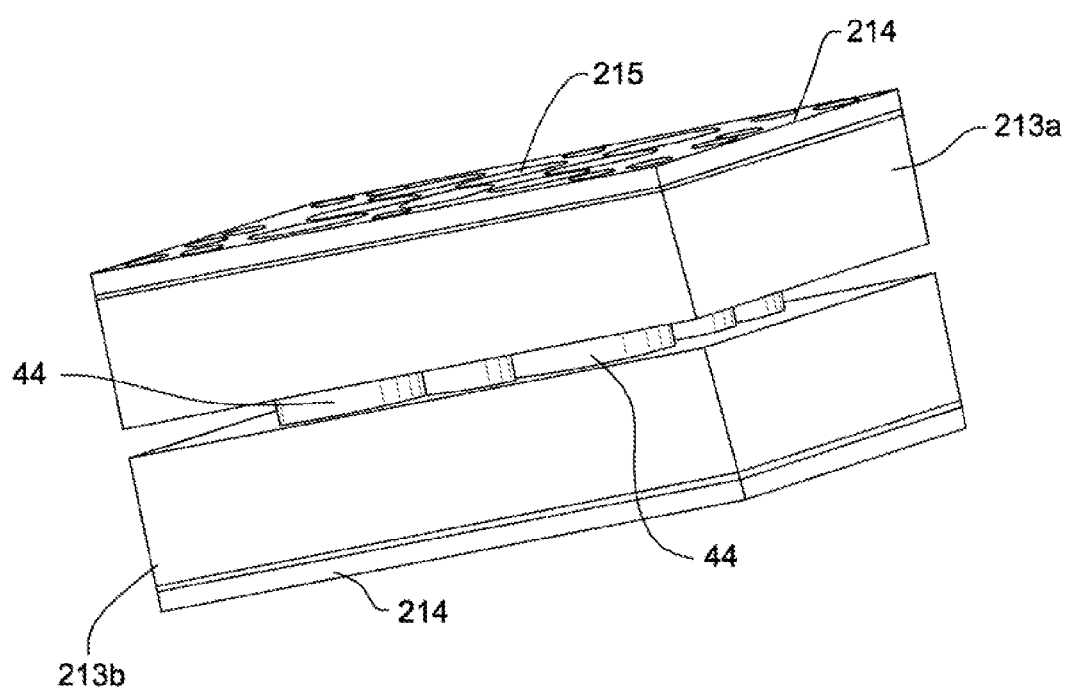
FIG. 15B is side view illustrating how the components forming the cell cluster are fitted in a pair of fixtures.

The second binder assembly 104 or 102 is then placed in its associated fixture 213b or 213a, respectively. As seen in FIG. 15B, the second fixture with fitted binder assembly is then fitted over the fixture assembly in which the binder assembly 102 or 104 and cells 44 are already placed.

Figure 16:
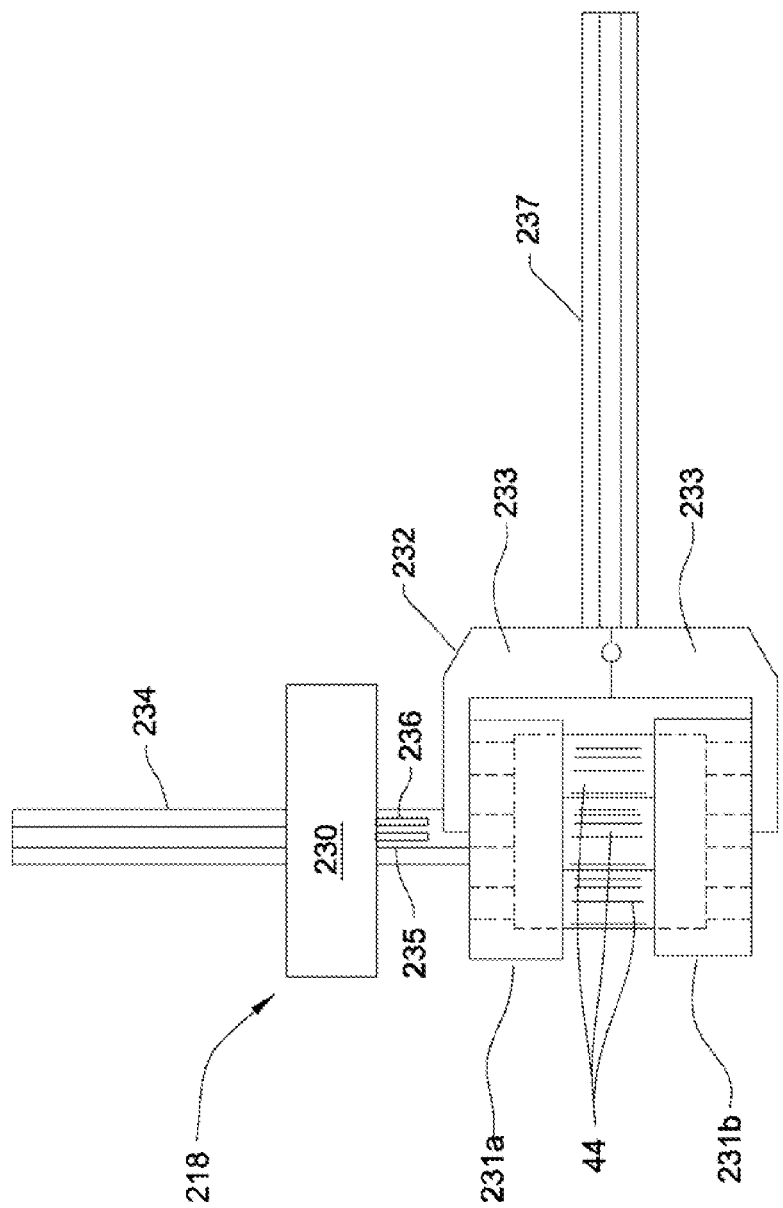
FIG. 16 is a diagrammatic illustration of the welding process used to complete the assembly of the cell cluster

A robotic welding unit 218, shown diagrammatically in FIG. 16, welds the conductive straps 106 and fuse 118 to the cells 44. Specifically, robotic welding unit 218 has a base 237 to which an arm 232 is attached. Arm 232 includes two opposed fingers 233 that, when brought together, clamp cells 44 and fixtures 213a and 213b therebetweeen. A drive mechanism, (not illustrated,) moves arm 232 and the components held thereby both in the X plane (to the left and right in FIG. 16) and in the Y-plane (in and out of the plane of FIG. 16).

Robotic welding unit 218 also includes a welding head 230. Head 230 is attached to a track 234 so as to be able to move in Z-plane, (vertically in FIG. 16). Two opposed electrodes 235 and 236 are attached to and extending downwardly from head 230.

The welding process begins with the placement of the sandwiched-between-fixtures cells 44 and binders 102 and 104 between fingers 233 of arm 232. Arm 232 is moved so that a first one of the fixture openings 215 is disposed below electrodes 235 and 236. Welding head 230 is lowered so that the electrodes 235 and 236 pass through the fixture opening 215 and the aligned binder opening 114 to the surface of the exposed conductive strap 106 (or fuse 118). Current is flowed between the electrodes 235 and 236 to weld the strap 106 (or fuse 118) to the surface of the underlying cell 44. Once this weld process is complete, head 230 is raised. Arm 232 is slightly repositioned so that when head 230 is again lowered, electrode 235 and 260 can make a second weld joint between the same strap 106 (or fuse 118) and cell 44.

After the two weld joints for the first strap (or fuse) cell interface are completed, head 230 is again raised. Arm 232 is again positioned so each strap- (or fuse-) and-cell interface is similarly welded.

The final assembly of the battery 40 begins with the seating of a shock absorber 217 seen in FIG. 3, in the base of the housing 60. The shock absorber 217 is formed from a compressible material such as a silicon rubber. Shock absorber 217 subtends the area subtended by the cell cluster 62. In some versions of the invention, the shock absorber 217 is, in an earlier step bonded to the exposed face of the bottom binder assembly 104. Cell cluster 62 is placed in the housing. The connections are made between the cell cluster 62 and conductors 176 and wire assemblies 177.

Figure 17:
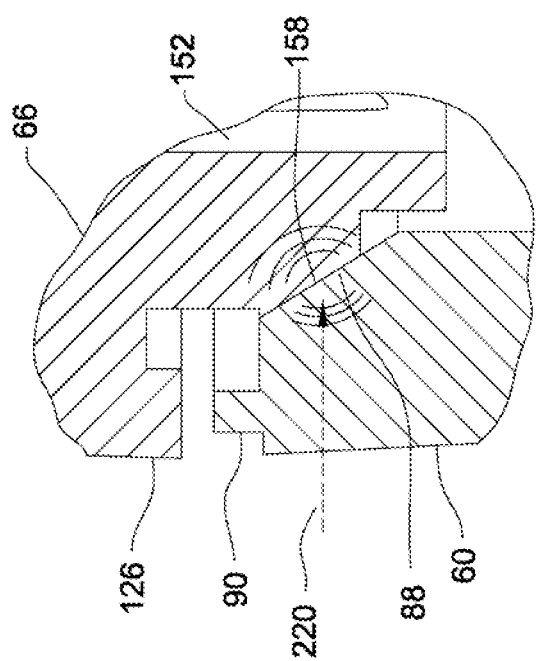
FIG. 17 is a cross sectional view of the interface of the battery housing and battery lid prior to the welding of these components together.

Lid 66 is then welded to the housing 60 to complete the assembly of the battery 40. In this process, the lid 66 is seated on the housing so that lid tapered surface 158 abuts housing tapered face 88. As seen in FIG. 17, owing to the dimensioning of housing 60 and lid 66, at this time, the lid is positioned so that the bottom horizontal surface of the lid base 126 is spaced above the housing reveal 90.

Figure 18:
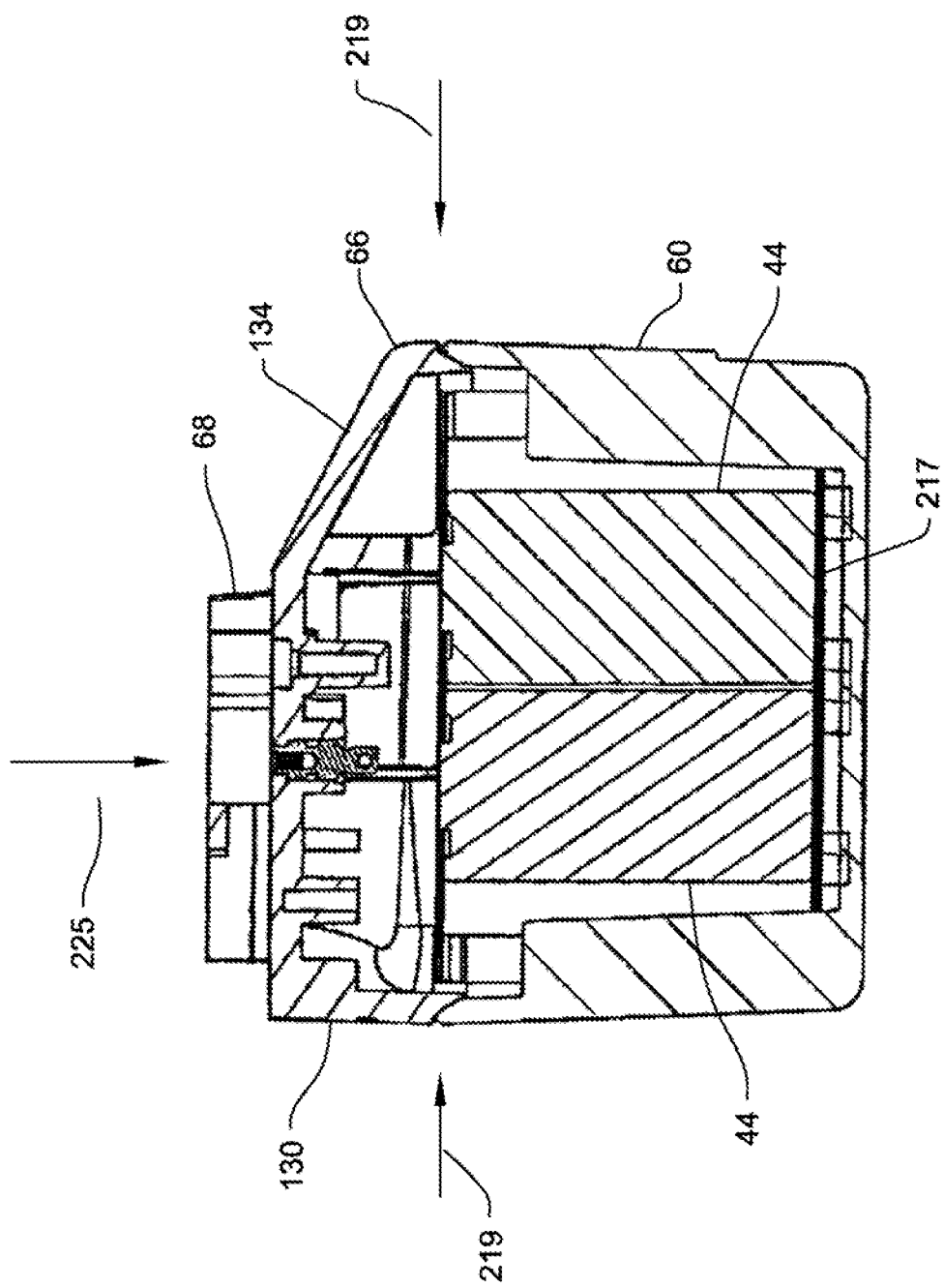
FIG. 18 is diagrammatic representation of how the battery housing and lid are welded together.

The welding process is accomplished by applying a downward force on the lid 66 so that the lid bears against the housing 60. In FIG. 18, this is represented diagrammatically by arrow 225. More particularly, owing to the angled profile of housing tapered surface 88 and lid tapered surface 158, these surfaces 88 and 158 abut. Simultaneously with application of the downward force, coherent (laser) light at 980 nanometers is simultaneously applied to the lateral section of the housing that subtends the interface between housing tapered face 88 and lid tapered surface 158. As represented by plural arrows 219, this photonic energy is applied simultaneously around the whole of the perimeter of the outer housing. A suitable system capable of performing this welding is available from Branson Ultrasonics of Danbury, Conn.

Owing to the transmissivity of the material forming the housing 60 to this wavelength of photonic energy, the energy passes substantially through the housing lip 84 as represented by phantom arrow 220 of FIG. 17. This energy is absorbed by the material forming lid lip 152. The material forming lid lip 152 thus heats to its melting point. This includes the material forming lid tapered surface 158. Owing to the downward force imposed on the lid 66, the lid therefore settles downwardly into the open space of the housing 60. The settling of lid 66 stops by the abutment of the bottom surface of lid base 126 against housing reveal 90.

Figure 19:
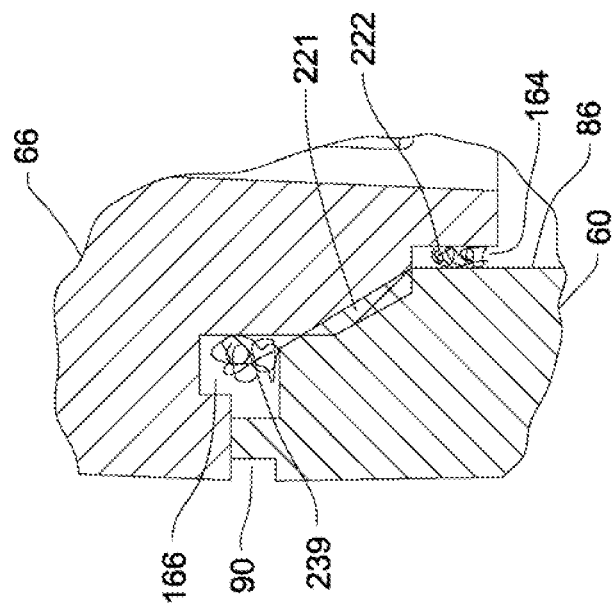
FIG. 19 is a cross sectional view of the interface of the battery housing and battery lid after the welding process.

Moreover, thermal energy is transferred from the lid tapered surface 158 to the adjacent abutting housing tapered surface 88. As represented to FIG. 19, this causes the material forming the housing tapered face 88 to likewise melt. Collectively, the material forming the opposed housing tapered face 88 and lid tapered surface 158 form a hermetic weld joint 221 around and along the interface of the battery housing 60 and lid 66.

It should be appreciated that, as part of the above process, a small amount of the material forming the housing tapered face 88 and lid tapered surface 158 spread away from these two surfaces. Some of this material, flash material 239 in FIG. 19, flows into the space immediately inward of housing reveal 90 and the contiguous lid notch 166. Other of this material, flash material 222, flows into the space between housing vertical surface 86 and lid lip outer vertical surface 164.

III. Charger

Figure 20A:
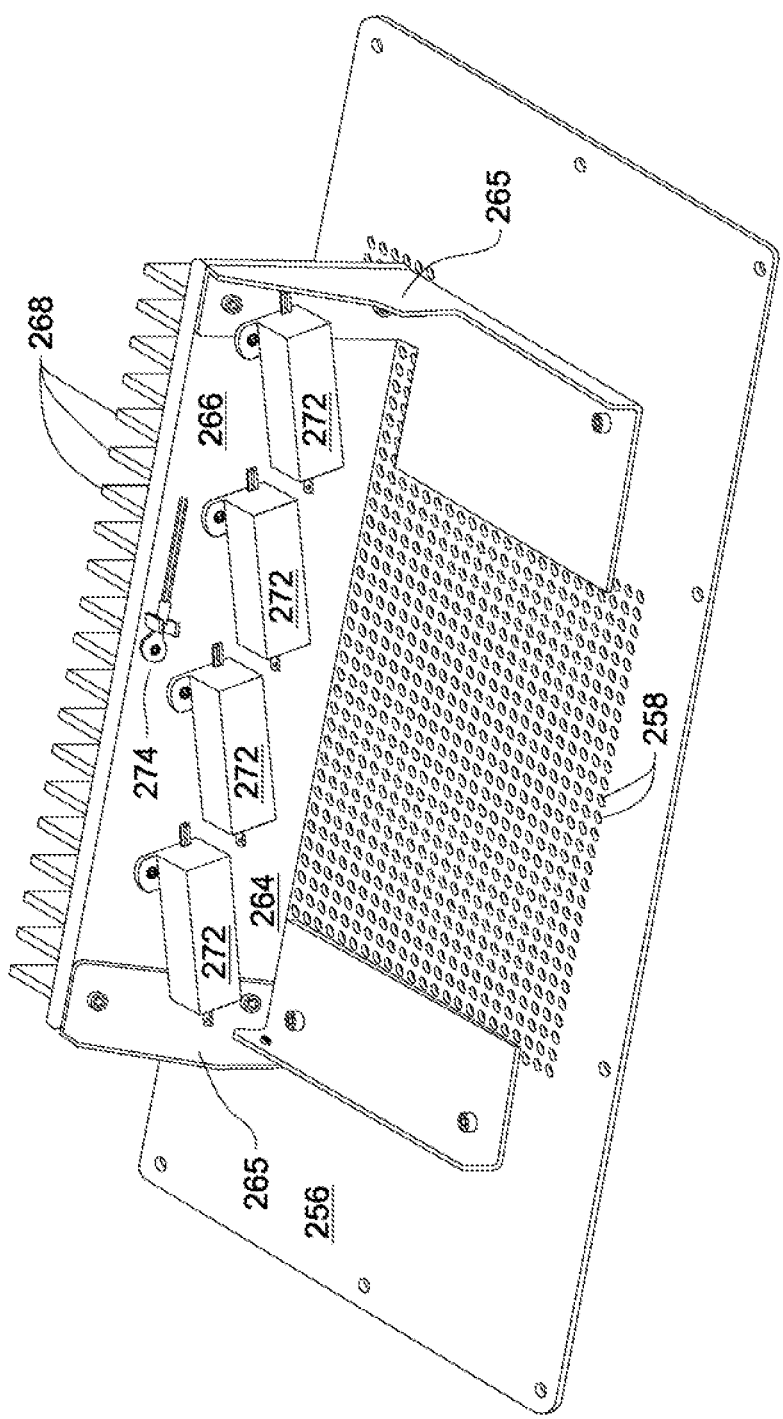
FIG. 20A is a perspective view of how the discharger resistors and complementary heat sink are secured to the charger base.
Figure 21:
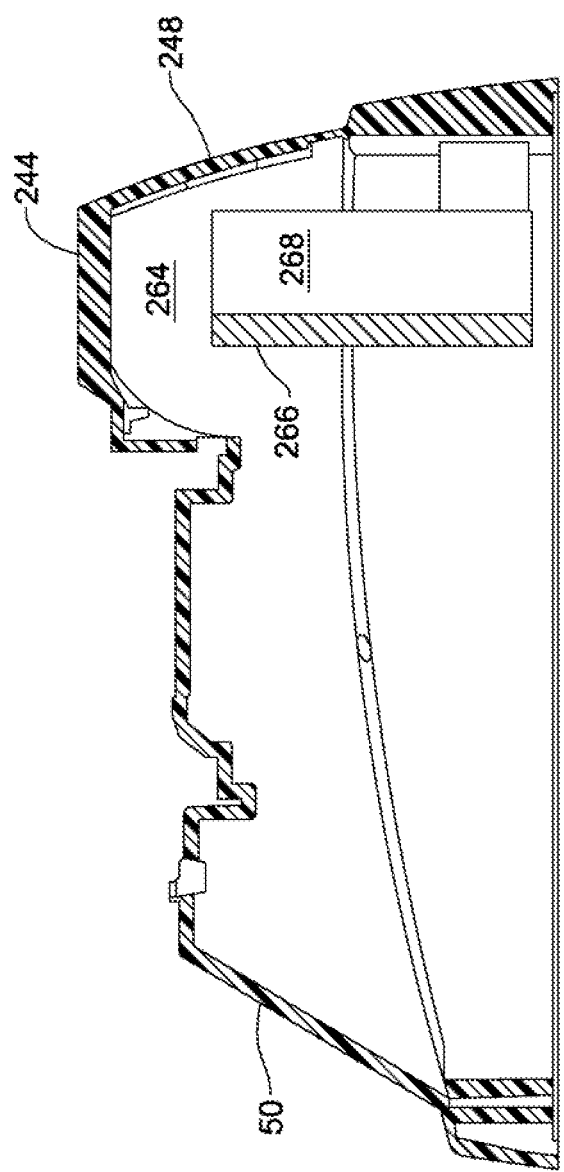
FIG. 21 is a cross sectional view of some of the components internal to the charger.

The basic structure of the battery charger 42 is now explained by reference to FIGS. 20, 20A and 21. Pockets 52 are formed in a front flat portion of the charger housing 50, (flat portion not identified). The charger housing 50 is further formed to have a back section 242 that is raised relative to the section in which pockets 52 are formed. A rear wall 244 forms the rear end of section 242 and thus, the rear end of the charger housing 50. Housing rear wall 244 is formed with a set of lower and upper ribs 246 and 248, respectively. Both ribs 246 and 248 extend vertically. A web 250, part of housing rear wall 244, separates ribs 246 and 248 from each other. Ribs 246 are spaced apart from each other to define vertical vents 252 therebetween. Ribs 248 are spaced apart from each other to define vertical vents 254 therebetween.

Battery charger 42 also has a metallic, plate shaped base 256. In one version of the invention, the base 256 is formed from spring steel. Base 256 is disposed in the open end of housing 50. The base 256 is shaped to have numerous openings 258 that extend therethrough. Base 256 is the structural component internal to the charger to which the majority of other charger components are attached. Not seen are the structural components and fasteners that hold housing 50 and base 256 together.

One component attached to base 256 is a heat sink 264. In some versions of the invention, heat sink 264 is formed from aluminum or other material with good thermal conductivity characteristics. The heat sink 264 is shaped to have a planar base 266. A number of fins 268 extend perpendicularly outwardly from the base 266. Fins 268 extend laterally across the base 266.

The heat sink 264 is mounted to base 256 by brackets 265. More particularly, the heat sink 264 is mounted to the base 256 so that the heat sink is disposed within the space internal to housing back section 242. More particularly the heat sink 264 is positioned so that there is free space between the outer edges of the fins 268 and housing vents 252 and 254.

A set of discharge resistors 272 are mounted to the face of the heat sink base 266 opposite fins 268. As discussed below, during certain processes for charging or evaluating a battery 42, it is necessary to first fully discharge the stored energy in the battery. This process step is executed by connecting the battery to a discharge resistor 272. In the illustrated version of the invention, each discharge resistor 272 is associated with a separate one of the charger pockets 52. During the discharging of a battery 40, each battery is tied to the specific discharge resistor 272 associated with the pocket in which the module 54 to which the battery is coupled is seated.

Each discharge resistor 272 generally has a resistance of 15 Ohms or less. In still other versions of the invention, each discharge resistor 272 has resistance of 10 Ohms or less. Each discharge resistor 272 is often encased in its own heat sink, (not illustrated). This resistor heat sink is the resistor component that physically abuts the heat sink base 266.

Also attached to the heat sink base 266 is a temperature sensor 274. It will be observed there is no fan or other device internal to or otherwise integral with the charger 42 for moving air through the housing 50 or across the heat sink 264.

From FIG. 1 it is seen that each I/O unit 58 includes an LCD display 278 and two LEDs 280 and 282. Each I/O unit 58 of charger 40 of this invention further includes two membrane switches 284 and 286.

Figure 22:
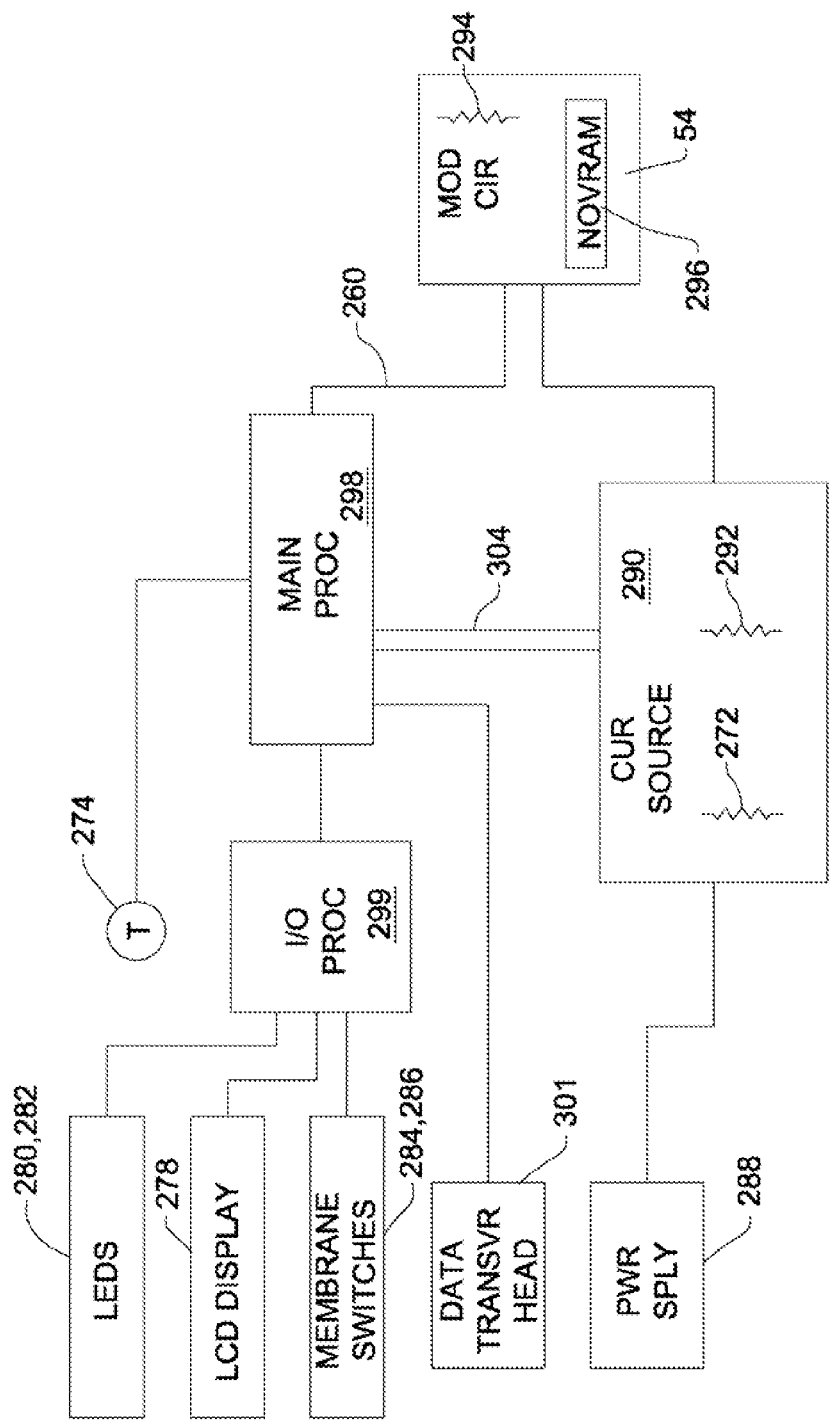
FIG. 22 is a block diagram of sub-circuits internal to the charger and a module attached to the charger.

FIG. 22 is a block diagram of the electric circuit assemblies internal to charger 42. A power supply 288 converts the line current into signals that can be used to energize the other components internal to the charger 42. Power supply 288 also produces a signal that is applied, through a module 54 to the battery 40 to charge cells 44.

The charging current is applied to the battery by a current source 290. In actuality, charger 42 has plural current sources 290; one to apply current to a battery through each module 54. This allows different charging signals to be applied to simultaneously to separate attached batteries. For simplicity, only a single current source 290 is illustrated. Integral to each current source 290 is a resistor 292. When the battery 40 is seated in module 54, resistor 292 establishes a connection between the battery positive terminal and ground. Each discharge resistor 272 is associated with a separate one of the current sources. Thus, in FIG. 22, the discharge resistor 272 is shown internal to the current source 290. Each discharge resistor 272 has one end selectively connected to ground. The opposed end of resistor 272 is selectively tied to the battery positive terminal by a switch, typically a FET (switch not shown).

Module 54, one shown as a block element in FIG. 18, also includes a resistor 294. Resistor 294 is selectively connected across the terminals to which battery contacts 70 are connected. A switch, typically a FET (not illustrated) is used to make this connection. Resistor 294 is thus used to measure the voltage at load of the battery 40.

The module 54 also contains a NOVRAM 296. NOVRAM 296 contains charging sequence and charging parameter data used to regulate the charging of the battery 40 charged through the module. A main processor 298, also internal to charger 42, controls the charging of the battery 40. Main processor 298 further determines, if it is necessary to perform a state of health evaluation of a battery, performs the evaluation and, based on the data generated in the evaluation, generates an indication of the state of health of the battery. Main processor 298 also generates the read/write instructions to obtain data from and load data into the memory integral with battery microcontroller 46 and module NOVRAM 296. In one version of the invention, the AT91SAM7X256/128 available from Atmel of San Jose, Calif. functions as the main processor 298.

More specifically, the main processor 298 is connected to the current source 290 over a plurality of conductors collectively represented as bus 304. Main processor 298 outputs a variable CURRENT_CONTROL signal to the current source 290. In response to the CURRENT_CONTROL signal, current source 290 outputs a charging current, at a select current, through module 54 to the battery cells 44. The voltage across resistor 292 is output over bus 304 to the main processor 298 as a MEASURED_VOLTAGE signal. This MEASURED_VOLTAGE signal is representative of the voltage across the battery 40. Also output from the main processor 298 through bus 304 is the signal to the switch that selectively ties resistor 272 to the battery 40. This connection causes the charge stored in the battery 40 to be discharge by the resistor 272.

Main processor 298 is connected to the module 54 by a plurality of conductors represented as a single-wire bus 260. Main processor 298 selectively generates the control signal that connects resistor 294 across the positive and negative terminals of the battery 40. When resistor 294 is so connected, the resistor 294 is connected to resistor 292. The MEASURED_VOLTAGE signal from the current source 290 thus becomes a measure of the voltage at load of the battery 40.

Bus 260 also functions as the link through which the contents of the module NOVRAM 296 are written to main processor 298. Data are also read from and written to the battery microcontroller 46 over bus 260.

The output signal produced by temperature sensor 274 is applied to the main processor 298.

Figure 26:
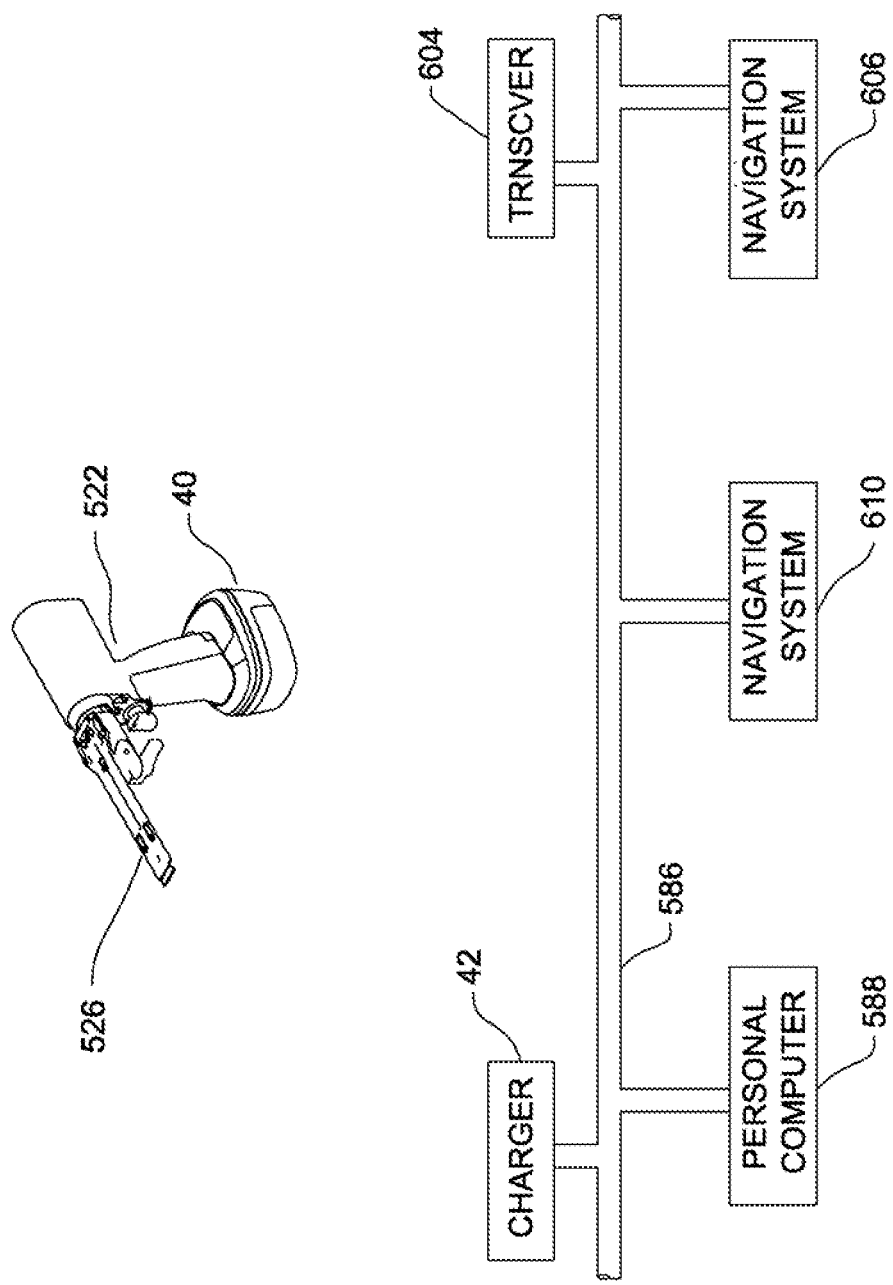
FIG. 26 is a block diagram illustrating of the tool communications system of this wherein the battery and charger are used to facilitate the exchange of data between the surgical tool and other components.

Main processor 298 is also connected to a data transceiver head 301. Transceiver head 301 is the interface internal to the charger connected to bus 586 (FIG. 26).

A more detailed description of the components internal to module 54 and current source 290 as well as the processes by which a battery may be charged is disclosed in the incorporated by reference U.S. Pat. No. 6,018,227. Additional description of the processes involved in charging plural batteries and alternative charge assemblies are found in the Applicants' Assignee's U.S. Pat. No. 6,184,655, Battery Charging System With Internal Power Manager, issued 6 Feb. 2001, the contents of which is incorporated herein by reference.

Battery charger 42 also contains an I/O processor 299. The I/O processor 299, based on signals output from the main processor 298, generates the signals that cause LCD display 278 to generate the appropriate image. The I/O processor 60 also regulates actuation of the LEDs 280 and 282. Membrane switches 284 and 286 are also connected to the I/O processor 299. Based on the signal generated as a consequence of the opening and closing of switches 284 and 286, the I/O processor 299 generates the appropriate commands to the main processor 298.

IV. Operation

A. Battery

Battery microcontroller 46 operates in three different modes. This is to minimize the load the components internal to the battery 40 place on cells 44. In a normal mode, all subcircuits internal to the microcontroller 46 are energized. In one version of the invention, when microcontroller 46 is in this state, it draws approximately 6 mA. Microcontroller 46 also has a power down, clock on state. When the microcontroller 46 is in this state, CPU 185, analog comparator 191 and the analog to digital circuit 192 are deactivated. Both the CPU clock 189 and the real time clock 190 are on when microcontroller 46 is in the power down, clock on state. When microcontroller 46 is in the power down, clock on state, the microcontroller draws approximately 3 mA.

A power down, clock off state is the lowest power consuming state in which microcontroller 46 operates. In this state, the CPU 185, the CPU clock 189, the real time clock 190 and the analog to digital circuit 192 are deactivated. When microcontroller 46 is in this state, the analog comparator 191 is activated. When microcontroller 46 is in the power down, clock off state, it draws approximately 120 to 150 μA.

It should further be appreciated that during the states in which the analog comparator 191 is on, switches internal to microcontroller 46 are set so there is current flow through resistors 209 and 210 to ground. This results in a $V_{TEMP\_REF}$ signal appearing at the inverting input of the comparator. When the analog comparator 191 is turned off, when battery microcontroller 46 is in the power down, clock on state, the microcontroller switches are set so both resistors 209 and 210 are tied high. This eliminates current draw of these resistors.

Figure 23A:
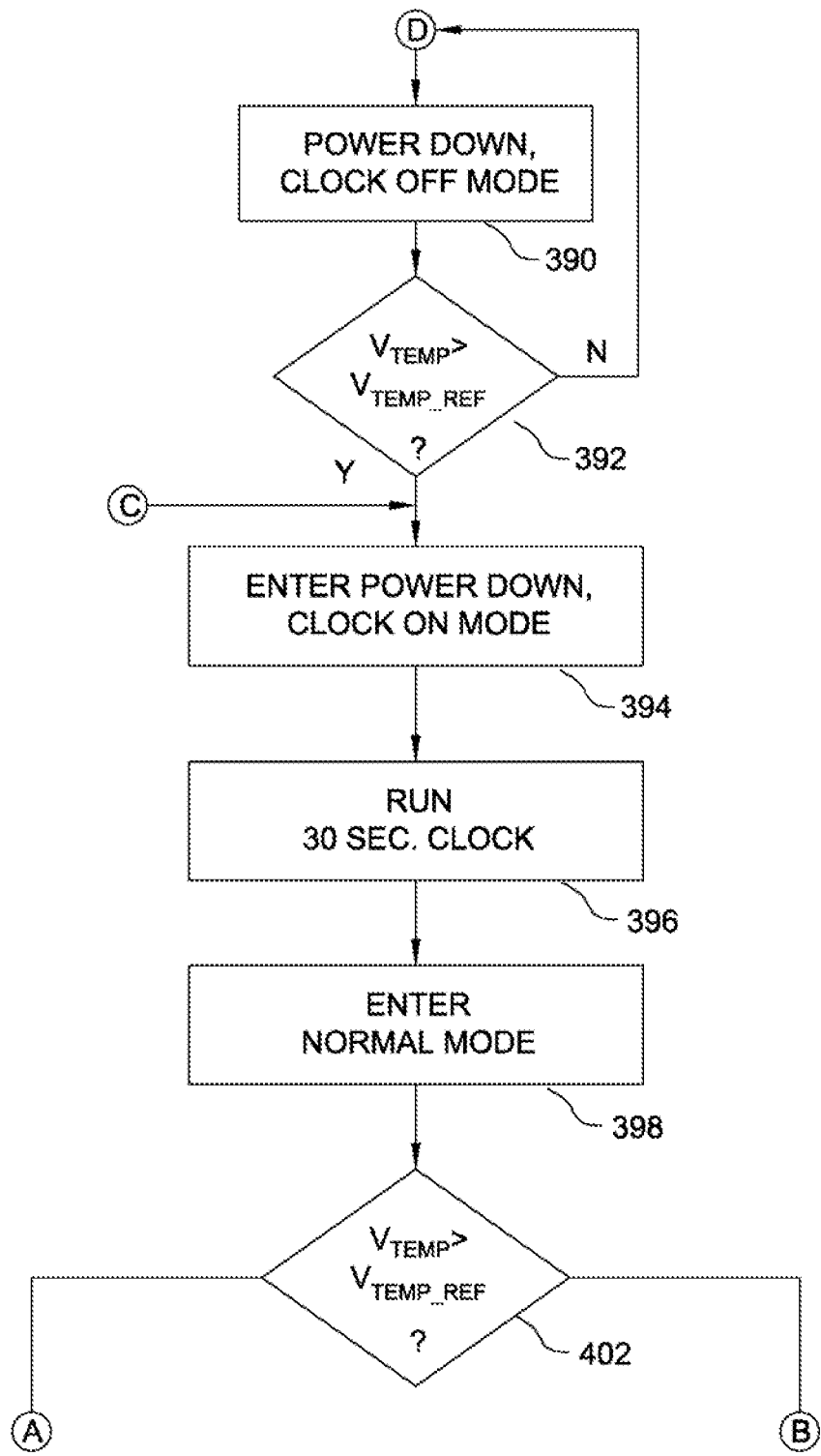
FIGS. 23A and 23B collectively form a flow chart of the process steps performed by the battery microcontroller to monitor the autoclaving of the battery.
Figure 23B:
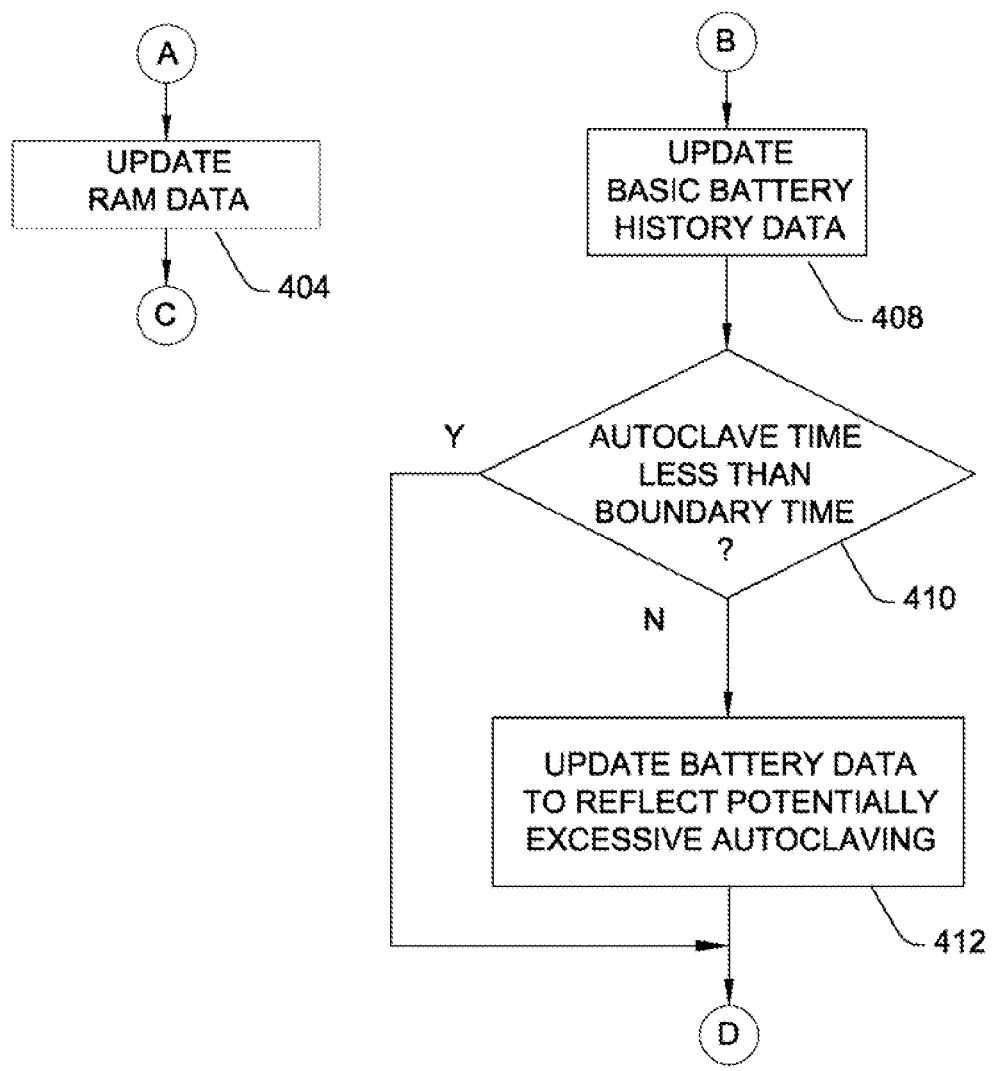

The operation of microcontroller 46 is now explained by reference to the flow chart of FIGS. 23A and 23B. For the majority of the time, battery microcontroller 46 is in the power down, clock off state. In FIG. 21A this is represented by step 390, the microcontroller entering the power down, clock off state. When microcontroller 46 is in this state, analog comparator 191 continually compares the $V_{TEMP}$ to $V_{TEMP\_REF}$, step 392. As long as this comparison indicates that signal from temperature sensor 48 indicates that the battery is not being autoclaved, microcontroller 46 remains in the power down, clock off state.

It should be appreciated that the reference signal $V_{TEMP\_REF}$ may not be a signal that corresponds to the actual temperature inside the autoclave. Instead to compensate for the thermal insulation of the battery housing 60 and lid 66, the $V_{TEMP\_REF}$ may be at a level that corresponds to a temperature less than that of the actual autoclave temperature. In some versions of the invention, the $V_{TEMP\_REF}$ signal is set to level to be representative of an autoclave temperature, generally this is an ambient temperature, of at least 100° C. Often, this is an ambient temperature of between 100 and 150° C. In alternative versions of the invention, it may be desirable to set the $V_{TEMP\_REF}$ signal so that the battery is considered in a harsh environment when in environment when the ambient temperature is at least 70° C. The actual level of the $V_{TEMP\_REF}$ signal may be determined by thermal modeling and/or empirical analysis.

If, in step 392, the comparison indicates that $V_{TEMP}$ is above $V_{TEMP\_REF}$, microcontroller 46 interprets $V_{TEMP}$ signal as indicating that the battery is being subjected to autoclaving. In response to this event, microcontroller 46, in step 394, enters the power down, clock on mode.

As a result of the microcontroller 46 entering the power down, clock on mode, the real time clock 190 counts down a 30 second time period, step 396. At the conclusion of this count, the microcontroller 46 transitions to the normal mode, step 398. Once in the normal mode, in a step 402, using comparator 191 again compares $V_{TEMP}$ to $V_{TEMP\_REF}$.

If the comparison of step 402 indicates that the battery is still being autoclaved, CPU 185 performs a data update step 404. In step 404, data stored in RAM 188 are updated. These data include a field that indicates the total time the battery has been at autoclave temperature. In some versions of this invention, the data in this field is simply incremented by a unit count (one unit=30 sec.). Also data in a RAM field that indicates the highest temperature of the current autoclave cycle may be updated. In this part of step 402, a digital signal representative of the $V_{TEMP}$ from the analog digital converter 192 are compared to the stored temperature level in the RAM 188. If the data from converter 192 is representative of a higher temperature than the stored measurement, these data are overwritten into the RAM field.

Once step 404 is executed, microcontroller 46 reenters the power down, clock on mode. Thus steps 394, 396 and 402 are reexecuted.

Upon completion of the autoclave process, battery temperature will drop to below the autoclave temperature. This event will be indicated by a different result in the comparison of step 402. Battery microcontroller 46 then updates the data stored in memory 187. This process includes an updating of the basic history data stored in memory 187, step 408. As part of step 408, then count of the number of times the battery has been autoclaved, the data in field 199 is incremented by one. Based on the data in the RAM 188 indicating the total time the battery was autoclaved, the data in the cumulative autoclave time field 200 is likewise revised. Also in step 408, the data in field 204 is updated to indicate the time the battery was, in this last autoclaving, autoclaved.

In step 408, the data in memory 187 are updated based on the RAM data indicating the total time the battery was, in this autoclaving autoclaved. Specifically, data indicating the total time the battery was autoclaved in this cycle are written into field 205. The data in field 206 indicating the peak single autoclave time is, if necessary, likewise rewritten. In some versions of the invention these data are first written into the RAM.

In a step 410 microcontroller CPU 185 determines if the battery was subjected to a potentially excessive autoclaving. This step is performed by comparing from RAM 188 the time the battery was autoclaved to a boundary time. This boundary time is the limit of the acceptable time for which the battery can be autoclaved and there will not be any potential of damage to its internal components. In some versions of the invention, this boundary time is between 3 and 60 minutes. In still more preferred versions of the invention, this boundary time is between 5 and 30 minutes.

If the battery was not subjected to a potentially excessive autoclaving, microcontroller returns to the power down, clock off mode. Step 390 is reexecuted.

However, if the comparison of step 410 indicates that the battery may have been subjected to a potentially excessive autoclaving, there are further revisions to the data in a step 412. In step 412 the data in field 201 indicating the number of potentially excessive autoclaving to which the battery was subjected is incremented. In some versions of this invention these data are first written into the RAM 188. Then, in a single write-to-flash step, (not illustrated,) all the data written to the RAM 188 in steps 408 and 412 are written to the flash memory 187.

Also in step 412, the cumulative time to which the battery has been exposed to potentially excessive autoclaving is updated. This time count is first adjusted by subtracting from the total time of the battery was autoclaved the boundary time. Thus, if the battery was autoclaved for 12 minutes and the boundary time was 10 minutes, by subtraction the CPU 185 determines that for this autoclave cycle the battery was subjected to 2 minutes of potentially excessive autoclaving. This is the value added to the cumulative data stored in field 202. Step 390 is then executed to return battery microcontroller 46 to the power down, clock off state.

B. Charger

Figure 24A:
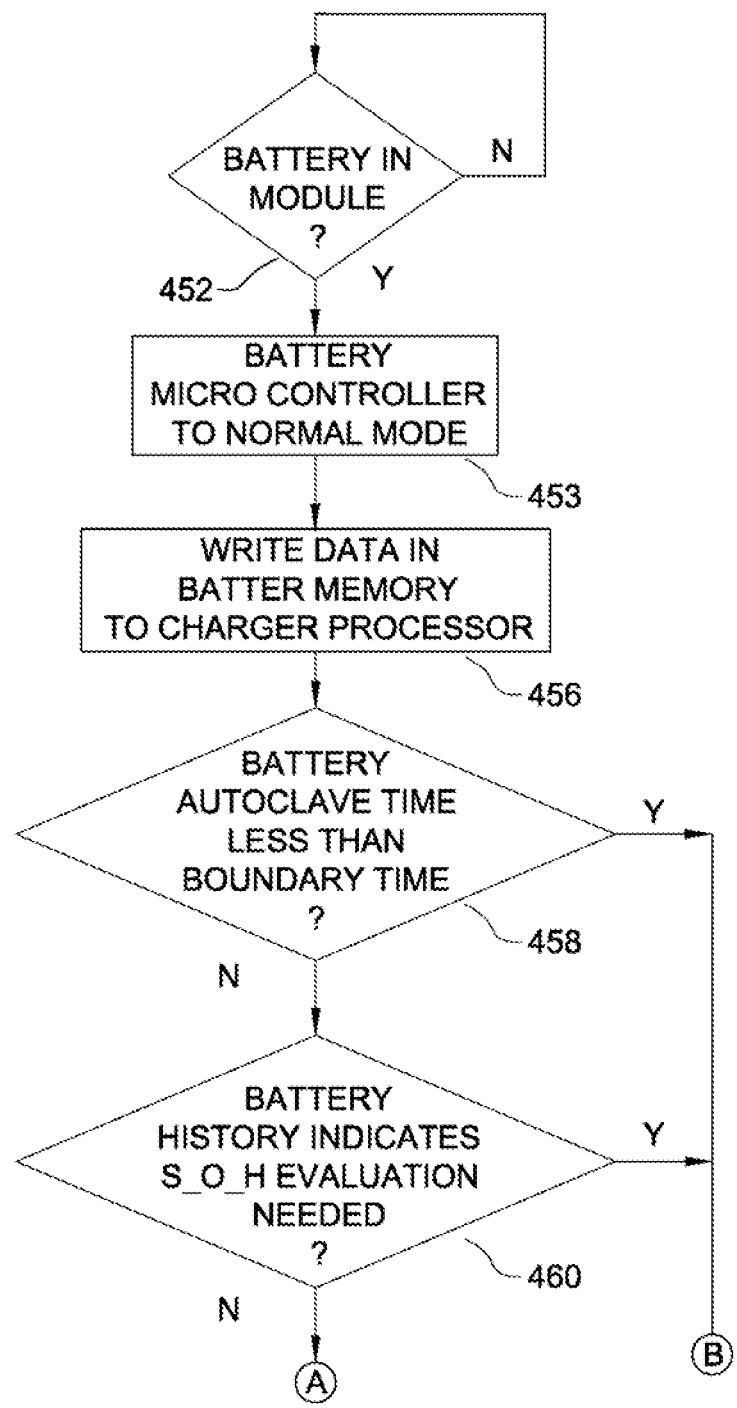
FIGS. 24A, 24B and 24C collectively form a flow chart of the process steps executed by the charger in order to charge a batter according to the process of this invention.
Figure 24B:
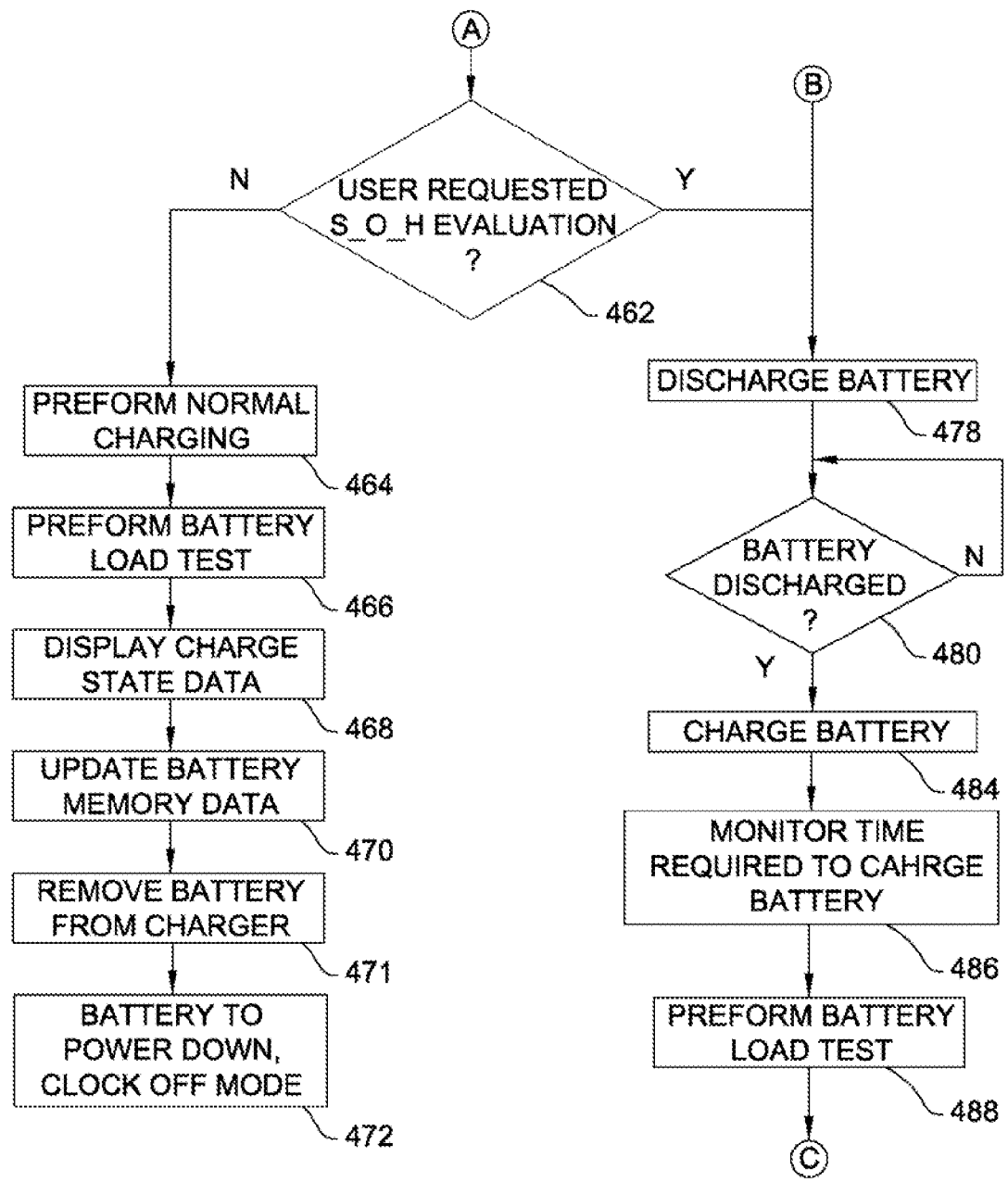
Figure 24C:
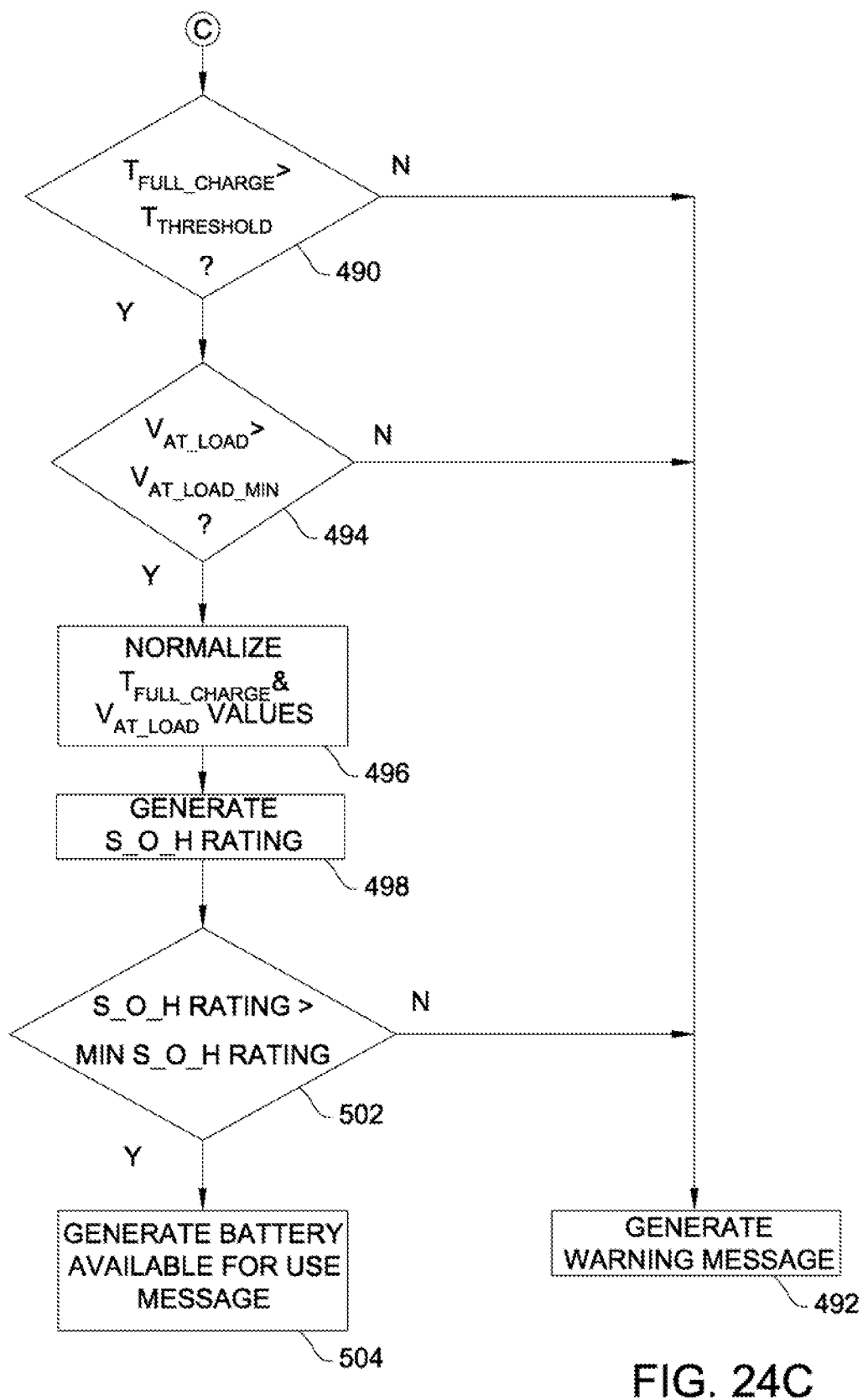

The process by which the charger 42 charges the battery is now 40 is now described by reference to the flow charts of FIGS. 24A, 24B and 24C. While not illustrated, it should be understood that the depicted process assumes the module 54 is seated in a charger pocket 52. Upon the seating of each module 54 in a pocket 52, the data in the module NOVRAM 296 are read to the charger main processor 298, (step not shown). In a step 452, main processor 298 continually tests to determine if a battery 42 is seated in a module 54. This test is performed by monitoring the level of the current source MEASURED_VOLTAGE signal. Specifically, if a battery is not seated in a module 54, the MEASURED_VOLTAGE signal is the open circuit voltage of the charging signal output by the current source. In some embodiments of the invention, this voltage is 20 VDC. As long as the MEASURED_VOLTAGE signal remains at the open circuit voltage level, main processor 298 continually reexecutes step 452.

The seating of a battery 40 in the module 54 causes the MEASURED_VOLTAGE signal to drop. In response to the drop in this signal level, (the seating of the battery in the module,) in a step 453 main processor 298 causes battery microcontroller 46 to transition from the power down, clock off mode to the normal mode. In one version of this invention, this transition is effected by tying battery contact 70 to ground for a given time period. This pulls the one-wire communication line connected to microcontroller 46 to ground. An interrupt circuit internal to battery microcontroller 46 (circuit not illustrated) continually monitors this communication line. The interrupt circuit interprets the extended low state signal on the communication line as indication that it should transition the microcontroller 46 from the power on clock off state to the normal state.

Once the battery microcontroller 46 is in the normal mode, main processor 298 generates an instruction through the module 54 to cause the battery microcontroller 46 to write out to the main processor 298 the contents of the associated memory 187. These data are written out to the main processor 298. The data written to the charger processor 298 include the charging sequence instructions and the data describing the use and autoclave history of the battery. Collectively, this read request and data write out are shown as step 456.

Main processor 298 then determines if the data retrieved from memory 187 indicates the battery should be subjected to a full state of health (S_O_H) evaluation. One test made to determine if the battery 40 should be so evaluated is, in step 458, the determination based on the data retrieved from memory file 204. The last entry in file 204 indicates the total time the battery was autoclaved in the last autoclaving. Main processor 298, in step 458 compares this value to the boundary time. If the last autoclaving was for a time more than the boundary time, the main processor 298 considers the battery to be in a state in which it is appropriate to perform a state of health evaluation.

As represented by step 460 other data read from the battery memory 187 are also tested to determine if a state of health evaluation is required. For example, in step 460 the data in the fields 196 and 199 are read to determine if, respectively, the battery has been subjected to more than P number of rechargings or Q number of autoclavings. Also in step 460 the data in field 202 are read to determine if, since manufacture, the battery has been subject to R amount of total time of potential excessive autoclave exposure. It should be appreciated that, in step 460, processor 298 determines it is necessary to perform a complete state of health evaluation if the battery has been subjected to a multiple of P rechargings, Q autoclavings or R total time of potentially excessive autoclave exposure.

Also once the charger processor 298 detects the battery is placed in the module socket 56, the processor may cause a message to be presented on the complementary display 278 asking if a state of health evaluation is wanted, (step not shown). The person responsible for charging the battery 40 indicates if the evaluation is required by depressing an appropriate one of the membrane switches 284 or 286, step 462.

If a state of health evaluation is not required, the charger executes a standard charging sequence for the battery, step 464. In step 464, based on the sequence instructions received from the battery microcontroller memory 187 or module NOVRAM 296, charger main processor 298 causes the connected current source 290 to apply the appropriate sequence of charging currents to the battery cells 64. It should be appreciated that the charging currents are also based on the MEASURED_VOLTAGE signals obtained from the current source 290.

Once the charging process is complete, charger 42 performs a voltage at load test on the battery, step 466. Typically, the voltage at load test is performed by measuring the voltage at load across the battery 40. Charger main processor 298 performs this evaluation by asserting the appropriate gate signal to FET integral with the module to which resistor 294 is attached (FET not illustrated). This results in the connecting of the module resistor 294 across the positive and negative terminals of the battery. As a result of resistor 294 being so connected to the battery, the MEASURED_VOLTAGE signal from the current source 290 becomes a measure of the voltage-at-load of the battery. Execution of this single test of battery state can be considered the performance of a partial state-of-health evaluation of the battery 42.

In a step 468, main processor 298, through I/O processor 299, causes an image to be presented on display 278 indicating the voltage at load of the battery. This data is sometimes referred to as an indication of the basic state of health of the battery. If the battery voltage at load (basic state of health) is at or above an acceptable level, main processor 298, again through the I/O processor 299, causes an appropriate one of the LEDs 280 or 282 to illuminate to indicate the battery is available for use, also part of step 468.

In a step 470, main processor 298 writes into battery memory 187 data regarding the charging. Specifically, in step 470 the count of the number of chargings stored in memory field 196 is incremented. Also data are added to file 197 to indicate the measured voltage-at-load of the battery after charging.

Eventually, the battery 40 is removed from the charger 42, step 471. As a consequence of this step, there is no communication over the one-wire line internal to the battery 40. The signal on this line transitions to a continuous high level state. As discussed above with respect to step 453, the signal level on this communications line is monitored by an interrupt circuit. The interrupt circuit interrupts the signal level of the communications line being high for an extended period of time as an indication that step 471 was executed. Therefore, in step 472, the interrupt circuit transitions the battery microcontroller from the normal state back to the power down, clock off state. Charger 42 returns to step 452.

While not shown, it should be understood that after the charging process is completed, main processor 298 also causes one of the LEDs to be appropriately actuated to indicate that the battery is available for use.

As represented by step 478, a battery full state of health evaluation starts with the complete discharging of the battery. Step 478 is executed by the main processor 298 asserting the appropriate gate signal to tie the battery positive terminal to resistor 272. Periodically, the voltage across the battery is measured, step 480. This step is executed until it is determined the battery is fully discharged.

Once the battery 40 is fully discharged, charger 42 proceeds to charge the battery, step 484. Step 484 is essentially identical to step 464. As part of this evaluation, main processor 298, in step 484, also monitors the overall length of time it takes for the cells 64 internal to battery to fully charge. As is known in the art, main processor typically determines the cells are full charged by determining when change in voltage over a period time falls to a value less than 0, (negative slope.) Thus, in step 486 during the primary or main state charging of the battery 40, main processor 298 monitors both the $\Delta V_{BATTERY}/\Delta_{Time}$ and the time from the start of the main state charging it takes for this slope to go negative. This time is $T_{FULL\_CHARGE}$.

Once the main state charging of the battery is complete, charger 42 performs a voltage at load test, step 488. Step 488 is essentially identical to the voltage at load test of step 466.

Based on the data obtain in steps 486 and 488, main processor 298 determines if the health of the battery is such that it can supply the amount of power needed to actuate a powered surgical tool. In a step 490, main processor 298 makes this determination by determining if the overall time it took the battery to fully charge, $T_{FULL\_CHARGE}$, is at or above a threshold time, $T_{THRESHOLD}$. The basis for this evaluation is that the $T_{FULL\_CHARGE}$ time is directly proportional to the quantity of charge being stored in the battery. Therefore, if $T_{FULL\_CHARGE} > T_{THRESHOLD}$, this is an indication that the quantity of charge in the battery is above that needed to energize a surgical tool for the total time such power is required. Thus, when the above determination tests true, main processor 298 recognizes the battery as being in state in which it most likely can power the surgical instrument as required.

If the determination of step 490 tests false, main processor 298 considers the battery to be in the opposite state. In this event, main processor 298 causes the I/O processor 299 to generate the appropriate fault state message, step 492, regarding the battery 40 on the display 278. This provides notice the battery may not function appropriately.

As part of the state of health evaluation, main processor 298 determines whether or not the voltage at load is above a minimum voltage value, step 494. If the battery voltage at load is not above this minimum value, the battery is considered to have an internal resistance so high that it cannot appropriately energize the tool to which it is attached. Therefore, if in a step 494 the determination tests false, step 492 is executed.

As part of the state of health evaluation, main processor 298 further determines whether or not the battery can deliver sufficient charge based on both $T_{FULL\_CHARGE}$ and the measured voltage at load. Specifically, both $T_{FULL\_CHARGE}$ and measured voltage at load values are normalized, step 496. In some version of the invention, each of these values is normalized by quantifying them to a range for example, between 0.0 and 1.0.

Then, in a step 498 the normalized $T_{FULLCHARGE}$ and $V_{ATLOAD}$ values are used as input variables into an equation. This equation may be a simple summation, $$S\_H\_R = T_{FULLCHARGE} + V_{ATLOAD} \tag{1}$$

Here S_H_R is state of health result. Alternatively, the normalized values are multiplied by coefficients $$S\_H\_R = A(T_{FULLCHARGE}) + B(V_{ATLOAD}) \tag{1a}$$

Here, A and B are constants. In some versions of the invention, the variables are multiplied together:

$$S\_H\_R = C(T_{FULLCHARGE})(V_{ATLOAD}) + D \tag{1b}$$

Here, C and D are constants.

Once S_H_R is calculated, in step 502, it is compared to a cutoff value, $S\_H\_R_{CUTOFF}$. If S_H_R is equal to or greater than $S\_H\_R_{CUTOFF}$, the charger main processor 298 recognizes the battery as being in a state in which it will deliver an appropriate charge to a surgical tool. Therefore, a step 504 is executed to cause the appropriate image to be presented on the display 282 and LED activation to indicate the battery is available for use. Also in step 504 the charger presents on display 278 an indication of the above calculated S_H_R result. These data are referred to as an indication of the calibrated state of health of the battery. If, in step 502 it is determined that the calculated S_H_R value is less than $S\_H\_R_{CUTOFF}$, step 492 is executed.

After either step 492 or 504 is executed, step 470 is executed to complete the charging process. (Not shown is the loop back to step 470.)

Figure 25:
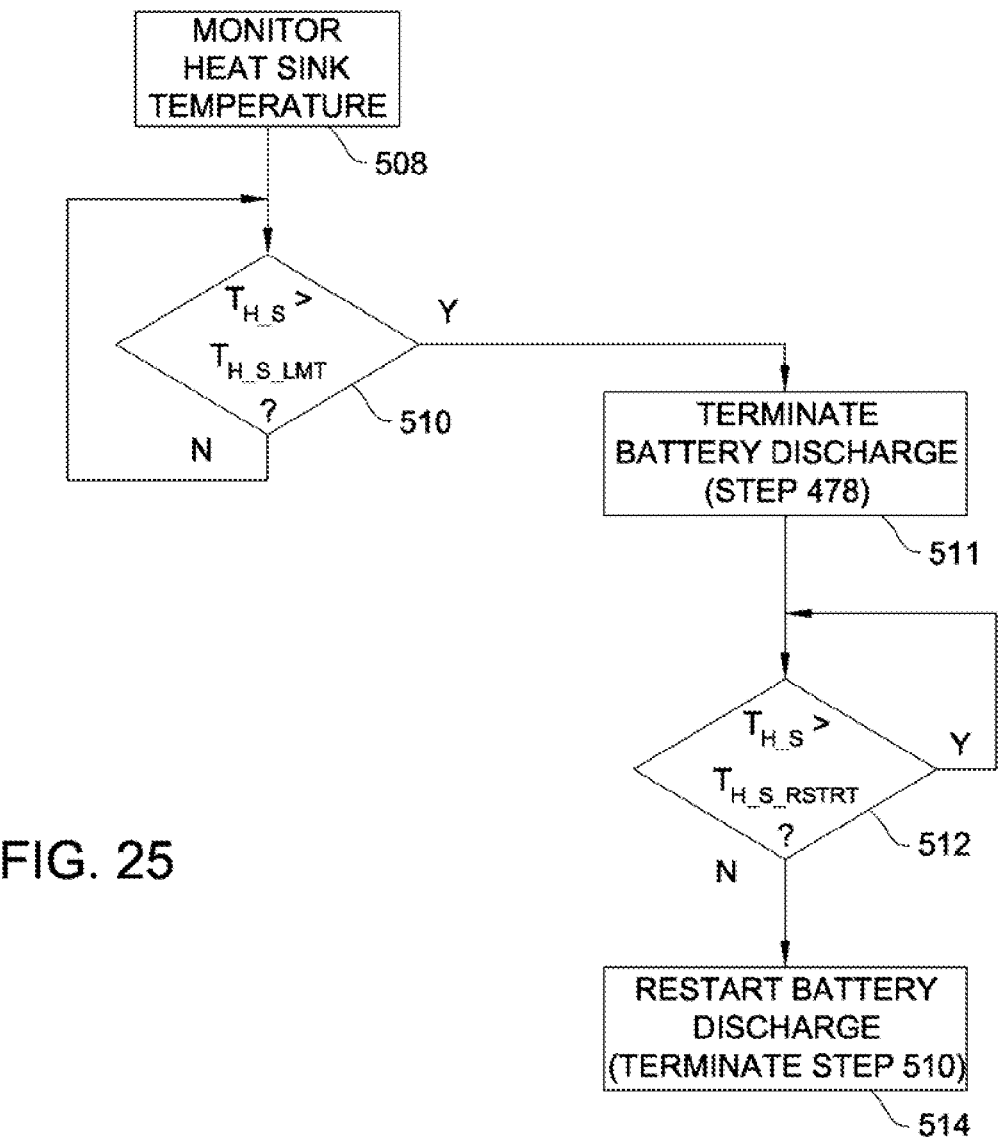
FIG. 25 is a flow chart of the process steps executed by the processor internal the charger to ensure that the charger temperature does not rise to potentially unsafe levels.

Charger 42 of this invention is further configured so that when actuated, temperature sensor 274 provides a signal to main processor 298 representative temperature of the heat sink 264. As represented by step 508 of FIG. 25, main processor 298 monitors the heat sink temperature, $T_{H\_S}$. As represented by step 510, the main processor compares the heat sink temperature to a limit temperature, $T_{H\_S\_LMT}$.

When charger 42 of this invention is required as part of a charging process or a state of health evaluation to discharge a battery 40, the battery charge is discharged through one of the resistors 272. The heat generated by this resistor is conductively transferred to heat sink 272. Most of the time air flow into the charger housing through base openings 258 and housing vents 252 has sufficient thermal capacity to sink the heat radiated by heat sink 272. This warmed air is discharged through housing vents 254. During such time periods the heat sink temperatures stays below the heat sink limit temperature.

However, there may be times the air flow past the heat sink 264 cannot sink all the heat sourced by the heat sink 264. This may occur if, due to unusual circumstances, the charger simultaneously discharges large amounts of current from plural batteries. If this event occurs, the measured rises heat sink temperature rises. If the heat sink temperature rises above the limit temperature, $T_{H\_S\_LMT}$, there is a possibility that further temperature rise will result in the charger housing 52 being heated to a temperature that makes it unpleasant, or worse, to touch the charger 42. The limit temperature, $T_{H\_S\_LMT}$, it should be appreciated, is often determined by empirical analysis.

Therefore, if the comparison of step 510 indicates the heat sink temperature is above the limit temperature, main processor 298 executes a battery discharge interrupt sequence represented by step 510. In this sequence, the charger interrupts the discharging of one or more attached batteries 40. Thus, in step 510, the discharge step 478 to which one or more of the batteries is presently being subjected may be interrupted. Similarly, if one of the batteries is being discharged as part of the normally charging sequence for that battery, that discharge step may likewise be interrupted.

Step 510 is executed until, as a result of a subsequent measurement of heat sink temperature, (step not shown) it is determined heat sink temperature has dropped below a restart temperature, $T_{H\_S\_RSTRT}$, step 512. Once the heat sink temperature is fallen to this level, additional thermal energy sourced by the discharged resistors 272 can be output without the likelihood of such heat placing the charger in an undesirable state. Therefore, once the heat sink temperature so drops, step 510 is terminated.

Battery 40 of this invention provides an indication if its cells may have been damaged. If the battery 40 may be in this state, charger 42 conducts a state of health evaluation on the battery. One immediate advantage of this invention is that, if the battery cells may have been damaged, a state of health evaluation is performed. This substantially reduces the possibility that someone will attempt to use a damaged battery to energize a surgical tool.

During the charging or discharging of the battery 40, the temperature of cells 44 inevitably rises. In this invention, each cell has some surface area that is spaced free of the adjacent cells. This minimizes the uneven heat dissipation and consequential uneven temperature rises of the cells. The reduction of this temperature imbalance results in a like lessening of the extent to which the individual cells 44 can become electrically imbalanced. Reducing the electrical imbalance of the cells reduces the extent to which the cells being so imbalanced can adversely affect either the utility or useful lifetime of the battery.

Battery 40 of this invention is also designed so that the narrow section 119 of fuse 118 is spaced from the adjacent binders 108 and 110. Section 119 is the section of the fuse 118 that vaporizes upon the flow of more than the selected amount of current flow through the fuse. Since fuse section 119 is not in physical contact with another section of the battery, no other section of the battery, such as the binders, serve as sinks for the heat generated by the current flow. Thus when the defined current flows through the fuse 118 the thermal energy generates in the vicinity of fuse section 119 stays in the section. This thermal energy therefore causes the fuse section 119 to rise to the level at which vaporization occurs. Thus, this design feature of the battery of this invention increases the likelihood that, when more than the defined current flows through the fuse, the fuse will open.

The charger 42 is further configured that it does not always perform the state of health evaluation, which can be time consuming to perform. Instead, the charger of this invention only performs this evaluation when the environmental history stored in the battery indicates it is desirable to perform the evaluation. By minimizing the number of times the charger performs state of health evaluations, the time it takes the charger to charge batteries is likewise held to a reasonable time period.

Still another feature of charger 42 is that the charger discharges batteries as part of a charging sequence or state of health evaluation yet it does not include a fan or other powered ventilation unit to exhaust air heated as a consequence of this discharging. The absence of fan in this charger reduces the noise generated by the charger when it is active. In the event there is an excessive generation of heat, further battery discharging is limited until the heat is dissipated.

Also battery 40 invention stores data regarding the environment to which the battery has been exposed. This information can be used to help evaluate why a battery underperforms and further provide feedback with regard to the charging and sterilization processes to which the battery is subjected.

Further, the laser welding assembly of the battery lid 60 to the underlying housing 66 eliminates the need to use fasteners to accomplish this attachment. Weld joint 221 formed by this process likewise eliminates the need to provide a separate seal to form an air-tight hermetic barrier between these components.

C. Tool Communication

Figure 27:
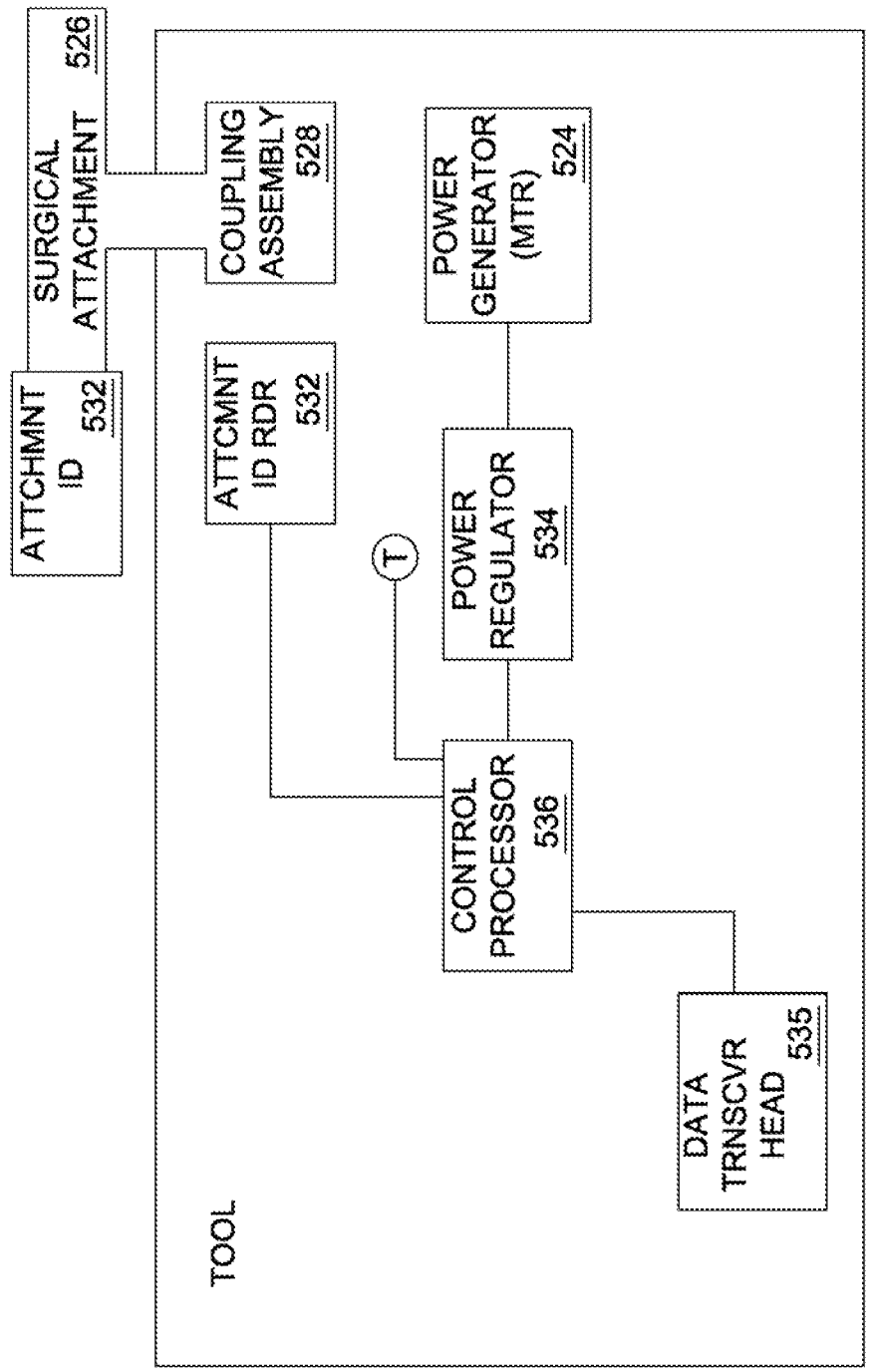
FIG. 27 is a block diagram of the components of tool of the system of this invention.
Figure 28:
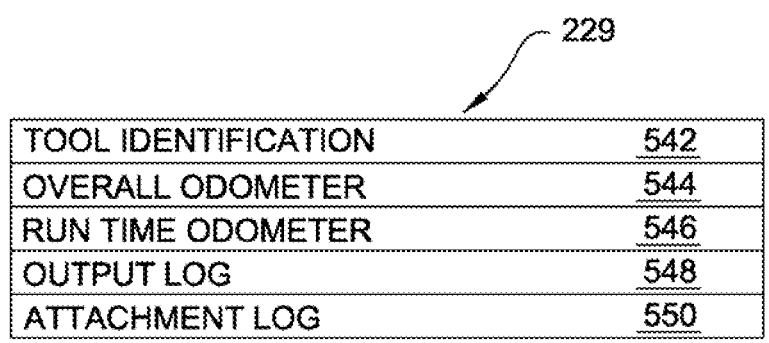
FIG. 28 is a block diagram of data stored in the tool history file internal to the battery microcontroller.

As depicted by FIG. 26, in a system 520 of this invention, battery 40 is used to energize a cordless powered surgical tool 522. The depicted tool 522 is a surgical sagittal saw. It should, of course, be recognized that the system of this invention is not limited to this type of tool or only tools with motors. FIG. 27 is a block diagram of components of tool 522 relevant to system 520 of this invention. Tool 522 has a power generator 524. The power generator 524 is the component internal tool 522 that actuates a surgical attachment 526. In the depicted invention, the power generator 524 is a motor; surgical accessory 526 is a saw blade. A coupling assembly 528 removably holds the surgical attachment to the tool 522. Integral with the attachment is identification component 530, such as an RFID. An attachment reader 532, part of tool 522 reads the data stored by the identification component 530.

A power regulator 534 selectively applies the energy output by battery 40 to the power generator 524. The power regulator 534 applies power to the power generator 524 based on instructions received from a control processor 536. Control processor 536 generates instructions to the power regulator 534 in part based on the depression of control members integral with the tool; (control members not illustrated). Control processor 536 receives from the attachment reader 532 the data read from the attachment identification on component 530.

Also internal the tool 522 is one or more sensors that monitor the operation of the tool. For simplicity only a single sensor a temperature sensor 538, is illustrated. When tool 522 includes a motor as the power generating unit, temperature sensor 538 is often placed in close proximity to a bearing assembly integral with the motor. The output signal generated by temperature sensor 538 is applied to tool control processor 536.

Tool 522 also has a data transceiver head 535. Head 535, which may be implemented in hardware or software, is designed to communicate with battery microcontroller 46. In one version of the invention, data transceiver head 535 consists of a software executed by tool controller 536 to exchange signals with battery microcontroller 46 and a contact integral with the tool 522 designed to establish a conductive connection with battery contact 72.

A more detailed description of the structure of a tool 522 integral with system 520 of this invention is found in the Applicants' Assignee's previously referenced U.S. Patent Application No. 60/694,592, POWERED SURGICAL TOOL WITH SEALED CONTROL MODULE, the contents of which are incorporated herein by reference.

During the use of tool 522 and battery 40 of this invention, data regarding the use of the tool are stored in the battery memory 187. More particularly, these data are stored in memory tool history file 229. FIG. 23 depicts in more detail types of data stored in the tool history file 229. A first file internal to file 229 is a tool identification file 542. File 542 contains data that identifies the tool 522 to which the battery 40 is attached.

Data regarding the total time the tool is run is contained in an overall run time odometer field 544. Data indicating the times the power generator 524 is run above or below specific operating state(s) is stored in one or more operating mode run time odometer fields 546. For example, if the tool power generator 524 is a motor, a first field 546 may store data indicating the overall time the motor is run at a particular speed. A second field 546 is used to store data indicating the overall time the motor is run under load. Tool control processor 536 makes a determination of whether or not the motor is run under load based on the current drawn by the motor. If the tool power generator 524 is a part of an ablation tool, an operating mode run time power generator field 546 stores data indicating the total time the tool is used to heat tissue to a particular temperature.

Tool history file 229 also contains a sensor output log file 548. File 548 is used to store data based on the signals generated by the sensor associated with the tool. In some versions of the invention, the data stored in file 548 are signals representative of the actual parameter sensed by the sensor. For example, if one sensor is a temperature sensor, the data in file 548 can include data indicating the peak temperature detected by the sensor. Alternatively, file 548 includes flags that are set as a function of the tool or environmental states sensed by the sensor. Thus, system 520 of this invention is set so that if the sensor 538 detects a temperature above a threshold level, a flag indicating that the tool reached such a temperature is set.

Also internal to tool history file 229 is an attachment log file 550. Accessory log file 550 contains data that identifies the specific attachment(s) 526 attached to the tool 520. These data are based on the data collected by the tool attachment reader 532. In some versions of the invention, each attachment file contains for each attachment, total run time odometer data, operating mode run time data and data based on the output from the sensors during use of the attachment.

Figure 29:
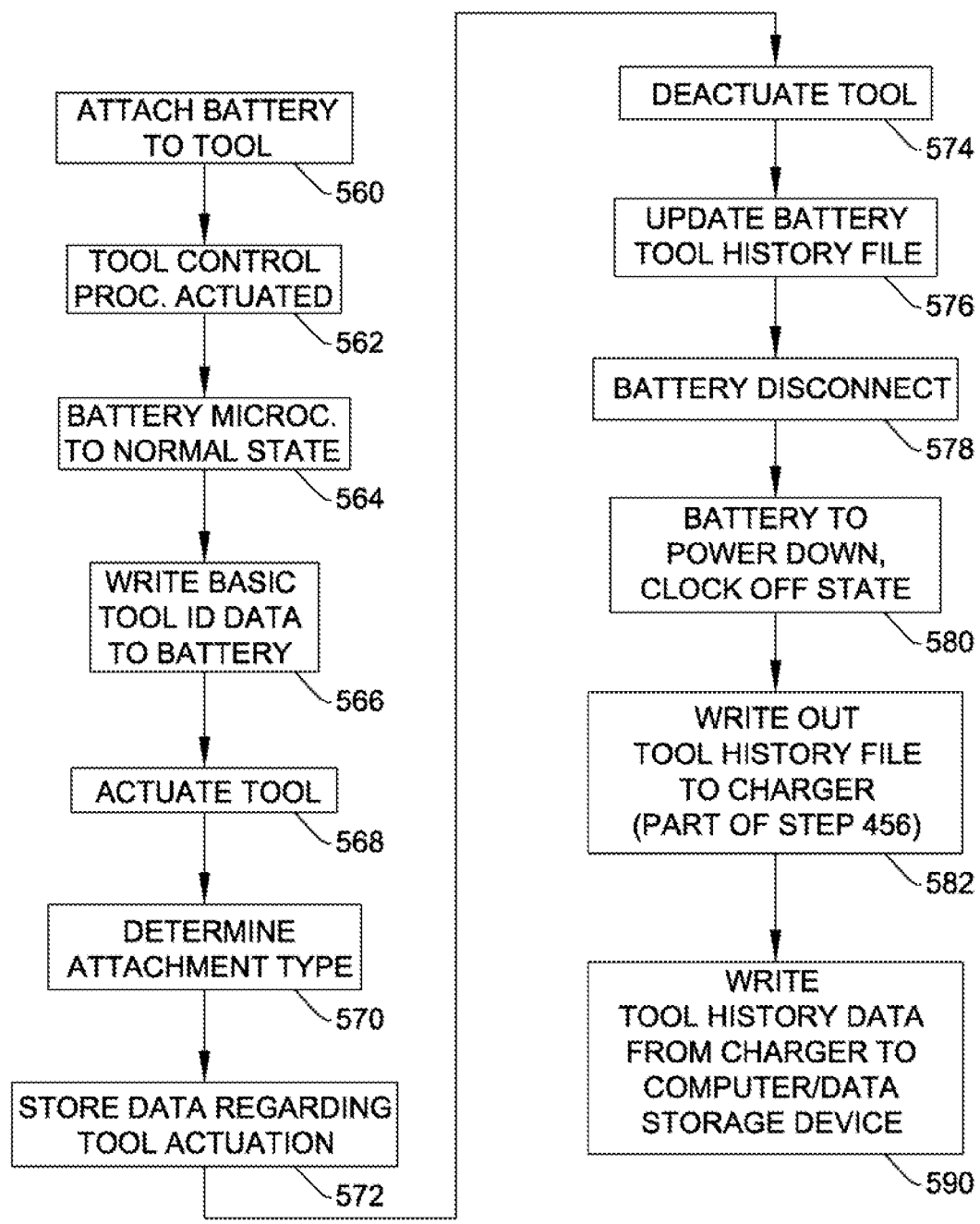
FIG. 29 is a flow diagram of the process steps executed in the tool communication system of this invention.

A process by which data are loaded into and retrieved from the battery microcontroller memory 187 are now described by reference to FIG. 29. Step 560 is the coupling of the battery to the tool. As a result of this step, there is immediate current flow to the tool and the subsequent actuation of the tool control processor 536, step 562. As part of the initial actuation sequence, tool control processor 536 pulls the one-wire communication line internal to the battery low so as to cause battery microcontroller 46 to transition from the power down, clock off state to the normal state, step 564. Tool control processor 536, in a step 566, then writes into battery microcontroller memory file 187 data identifying the tool.

Step 568 represents the actuation of the tool. At this time, tool control processor 536 engages in an initial collection of data regarding the operation of the tool, step 570. Step 570 involves determining from the attachment reader 532 the identity of the specific attachment 526 coupled to the tool. The data obtained in step 570, as part of the step, are stored in a RAM associated with the tool control processor 536 (RAM not shown).

As long as the tool continues to be actuated, tool control processor 536, in a step 572 acquires and stores data regarding the tool actuation. These data, for example, include total run time odometer data and data indicating run time in one or more states, for example, speed level, running at load or operating at a particular temperature. These data are likewise stored in the microcontroller RAM.

In a step 574 the tool is deactuated. In an immediate next step 576, tool control processor 536, through data transceiver head 535, updates the data log of the use of the tool in the battery microcontroller memory tool file 229. Thus, after each individual actuation of the tool, the data recorded in the odometer logs fields 544 and 546 are updated. It should be appreciated that not all of the data may be updated. For example, if peak temperature is measured during the first actuation of the tool, the temperatures reached in any subsequent actuations are not recorded.

Once use of the tool 522 is completed, battery 40 is disconnected, step 578. This results in battery one-wire communication line going high. This transition is detected by the interrupt circuit internal to the microcontroller 46. This signal staying high for an extended period of time is interpreted by the microcontroller as indicating the battery has been disconnected from the tool 522. Therefore, in a step 580, the microcontroller returns the battery to the low power consuming, power down, clock off state.

As discussed above with respect to FIG. 24A, once the battery is attached to the charger, in step 456, the data in the battery microcontroller memory 187 are written out to the charger main processor 298. As part of this process, the data in the tool history file are read out, step 582 of FIG. 29.

Returning to FIG. 26, it can be seen that the charger 42 is connected by a bus 586 to other components at the medical facility at which system 520 is installed. This connection is through charger transceiver head 301. The transceiver head 301 is the sub-circuit internal to the charger that allows charger processor 298 to exchange data and instructions with other components connected to bus 586.

The additional components connected to bus 586 include, for example, a personal computer 588. Thus in a step 590, the charger main processor 298 forwards the data in the battery memory tool history field 229 to another component on the attached network, for example the personal computer 588. Bus 586 may even have a telecommunication head (not identified). The telecommunications exchanges signal passed over the bus with signals on an external network such as a PSTN or external network.

This arrangement provides a log of the use of the cordless surgical tool 522 of the system 520 available to persons charged with maintaining the tool. For example, the data in the tool history file may indicate the tool reached a particular operating temperature. The occurrence of this event is recognized as indication the tool may require maintenance. In this event, a message regarding tool state may be transferred by the external network to an off site repair facility. Upon receipt of this notice, the repair facility can schedule the repair or replacement of the tool prior to the tool becoming inoperable. The data retrieved from tool history file 229 may likewise be used to provide information for warranty purposes or to ensure that, if the tool is approaching the end of useful life time, the relevant individuals receive notice of this fact.

V. Alternative Embodiments

It should be appreciated that the foregoing description is directed to one specific version of the battery and related components of the system of this invention. Other versions of this invention may have alternative features, constructions and methods of execution.

Thus, there is no requirement that each of the above inventive features be found in all embodiments of the invention.

For example, in some versions of the invention, the battery may not be sealed from the ambient environment. In these and other versions of the invention, the sensor internal to the battery may be one that is used to determine the exposure to an environmental agent other than temperature that could adversely affect charge storage by the cells 44. Thus, the sensor internal to the battery could detect humidity. If the sensor detects that the atmosphere within the battery is of relatively high humidity, data logging this event are stored in the battery memory. Another alternative sensor is an accelerometer. Such a device would record a rapid deceleration of the battery if it was dropped. Again, such an event would be logged in the battery memory. Then if the charger 42, upon reading the stored data, recognizes that the battery was exposed to the unusual environment event, the charger would subject the batter to the complete state-of-health evaluation.

Alternatively, an accelerometer or other sensor may be employed to sense whether or not the battery is excessively vibrated. Data regarding the excessive vibration is likewise stored in the battery memory.

With regard to the above it should also be understood that occurrence of one of the above environmental events may be the trigger that causes the battery to transition from the power down mode to the normal mode.

Further it should be appreciated plural such environmental sensor may be fitted to the battery.

Similarly, alternative constructions that come within the scope of the invention are also possible. Thus, a battery may be provided with cells having less or more than the eight (8) cells illustrated in the version of the invention illustrated in FIG. 6. For example, to provide a battery with ten (10) cells that has the heat dissipating cell arrangement of this invention, plural middle rows of cells, each having no more than two (2) cells per row may be provided. Also outer rows of cells with fewer or more than the three (3) cells may be provided depending on the number of cells the array is to have. In some versions of the invention, arrays of cells may be stacked one on top of the other.

Similarly, there is no requirement that in all versions of the invention the laser welding be performed using a laser that emits photonic energy at 980 nanometers. For example, in some versions of the invention, the laser welding may be performed with a laser that emits coherent light energy at 808 nanometers. Again, this is just exemplary, not limiting. It should likewise be appreciated that other medical equipment, not just batteries, may be laser welded using the process of this invention.

In this vein, it is further understood that there is no requirement that in all versions of the invention, the top of the housing always function as the component that is seated in the base and heated by the photonic energy. In other versions of the invention, this relationship may be reversed. Clearly, the laser welding may be used to assemble other components forming the housing together. Thus, the method may be used to secure multiple panels together.

Likewise, there is no requirement that the geometries along which the components forming the battery housing meet have the disclosed geometry. In some versions of the invention, either neither or only one of the surfaces along which the weld seam is formed may have a tapered profile.

Similarly, in some versions of the invention, the battery may only contain a non-volatile memory. When the battery is attached to the tool, the tool writes data to the memory. Then, when the battery is attached to the charger the charger reads out the data written into the memory by the tool so the data can be forward to the appropriate destination.

Clearly, there is no requirement that all versions of the invention be constructed to energize and communicate with powered surgical tools. Thus, the battery of this invention can be used to energize power consuming devices other than surgical tools. The communications system of this invention can be used to obtain data from devices other than cordless surgical tools.

It should likewise be appreciated that the components and process steps of this description are only exemplary and not limiting. For example, in some versions of the invention, the multiple components internal to the battery may function as the memory in which data are stored and the device that writes to and reads data from the memory. Likewise, in some versions of the invention, tool control processor 536 may, during actuation, simultaneously log data into the battery memory.

Circuit variations are also possible. Thus, in some versions of this invention, the end of resistor 209 opposite the $V_{TEMP\_REF}$ junction may be tied to the output pin of voltage converter 182. In these versions of this invention, the end of resistor 210 opposite $V_{TEMP\_REF}$ junction is tied to $V_{SS}$ or the BATT-terminal. An advantage of this version of the invention is that it results in a $V_{TEMP\_REF}$ signal that does not vary with manufacturing differences in microcontroller 46.

There is no requirement that all chargers of this invention be able to simultaneously charge plural batteries. There is no requirement a charger accept different modules so the charger is able to charger different types of batteries.

Also, it should be recognized that the power generator 524 need not always be a motor. The power generator may be a device that generates electrical energy, RF energy, ultrasonic energy, thermal energy or photonic energy.

Returning to FIG. 12, it can be seen that the battery may also be provided with a wireless transceiver 602. This transceiver may be an RF or IR unit. In some versions of the invention, the transceiver may be a Bluetooth transceiver. When the battery is connected to the tool, transceiver 602 exchanges signals with a complementary transceiver 604 attached to bus 586. Thus, this version of the invention allows real time communication between the cordless tool 522 and other operating room equipment through battery 40. For example using this arrangement, a voice actuated control head 606 can be used to regulate tool actuation. Thus, a command entered through control head 606 is packetized and sent over bus 586 to transceiver 604. Transceiver 604 broadcasts the command to battery transceiver 602. The command is transferred from the battery transceiver to the battery microcontroller 46. Microcontroller 46, in turn, forwards the command through the tool transceiver head 535 to the tool processor 530. Tool processor 530, in turn, generates the appropriate commands to the power regulator 534 to cause desired actuation of the power generator 524.

Similarly, a surgical navigation system 610 may likewise be connected to the tool through transceivers 602 and 604. The surgical navigation system tracks the position of the tool 520 and attachment 526 relative to the surgical site to which the attachment is applied. If the navigation system determines that the attachment is being position at a location at which it should not be used, the attachment would generate a stop command. This command is transmitted through transceiver 604 to transceiver 602 and, from transceiver 602, to the tool control processor 536. Tool control processor 536, upon receipt of the command, at least temporarily deactivates or slows operation of the tool 522.

It should likewise be understood that the not all batteries of this invention may be designed to withstand the rigors of sterilization. Alternatively, the features of this invention may be incorporated into an aseptic battery pack. This type of battery pack includes a sterilizable housing that defines a void space for receiving a removable cell cluster. A sealable lid associated with the housing allows insertion and removal of the cell cluster. With this battery pack, prior to sterilization, the cell cluster is removed from the housing. Thus the cells of an aseptic battery pack are spared the rigors of autoclave sterilization. The Applicants' Assignee's U.S. patent application Ser. No. 11/341,064, filed 27 Jan. 2006, ASEPTIC BATTERY WITH REMOVABLE CELL CLUSTER, now U.S. Pat. No. 7,705,559 B2, the contents of which are incorporated herein by reference, discloses one such aseptic battery pack. Still, the features of this invention may be built into the housing and or cell cluster of an aseptic battery pack.

Thus, it is an object of the appended claims to cover all such variations and modifications that come within the true spirit and scope of this invention.

What is claimed is:

1. A method of assembling a rechargeable battery, said method including the step of:
providing a first housing component, the first housing component formed from a polyphenysulfone plastic that does not appreciably interfere with the transmission of photonic energy at a select wavelength and that is formed to have an outer surface, an edge around the outer surface and an inner face that extends from the edge and is located inwardly from the outer surface;
providing a second housing component, the second housing component formed from a polyphenysulfone plastic that absorbs photonic energy emitted at the select wavelength and that is formed to have an outer surface and a lip that extends outwardly from and is located inwardly of the outer surface of the second housing component and wherein the first and second housing components are collectively shaped so that when the housing components are placed together: the lip of the second housing component abuts the inner face of the first housing component; and adjacent where the lip and the inner face of the first housing component abut there is a void, the void being located inwardly of the outer surfaces of the housing components;
placing at least one rechargeable cell in one of the housing components and connecting the cell to terminals mounted to one of the housing components;
placing the housing components together so the lip of the second housing component abuts the inner face of the first housing component;
directing photonic energy at the select wavelength towards the outer surface of the first housing component so that the photonic energy passes through the first housing component and is absorbed by the lip of the second housing component, so that:
the photonic energy heats the lip so as to cause the melting of the lip and the transfer of thermal energy to the first housing component so as to form a weld joint along the interface between where the lip of the second housing component abuts the inner face of the first housing component; and
flash formed by said welding flows into the void between the first and second housing components.

2. The method of assembling a rechargeable battery of claim 1, further including the step of placing a pressure on the housing components so that, during said welding step, the inner surface of the first housing component and the lip of the second housing component are pressed together.

3. The method of assembling a rechargeable battery of claim 2, wherein said step of placing a pressure on the housing components is performed simultaneously with said step of directing photonic energy at the first housing component.

4. The method of assembling a rechargeable battery of claim 1, wherein:
in said step of providing the first housing component, the first housing component that is provided is further shaped so that the inner face is tapered; and
in said step of providing the second housing component, the second housing component that is provided is further shaped so that the lip has a face surface that has a taper complementary to the taper of the inner face of the first housing component so that, as a result of said step of placing the housing components together, the tapered face surface of the lip of the second housing component abuts the tapered inner face of the first housing component.

5. The method of assembling a rechargeable battery of claim 4, wherein, simultaneously with said step of directing the photonic energy towards the outer surface of the first housing component, placing a pressure on one of the housing components so that the tapered inner face of the first housing component and the tapered face surface of the lip of the second housing component are pressed together.

6. The method of assembling a rechargeable battery of claim 1, further including the step of, prior to said step of placing the housing components together, placing a microcontroller that is powered by and connected to said at least one rechargeable cell in one of the housing components.

7. The method of assembling a rechargeable battery of claim 1, wherein:
in said steps of providing the first housing component and the second housing component: one of the first or second housing components is provided with a reveal that is spaced from where the weld joint between the housing components is formed and that is directed to an adjacent surface of the other one of the second or first housing components; the housing components are collectively shaped so that, as a result of performing said step of placing the housing components together, the housing component on which the reveal is not formed is spaced away from the reveal; and
during said formation of the weld joint, the housing components are urged together and the abutment of the housing components is stopped by the abutment of the housing component that is not formed with the reveal against the reveal.

8. The method of assembling a rechargeable battery of claim 1, wherein, as a result of said step of directing photonic energy towards the outer surface of the first housing component, the weld joint that forms between the housing components is a hermetic weld joint.

9. The method of assembling a rechargeable battery of claim 1, wherein, in said step of providing the second housing component, the second housing component that is provided contains a dye, the dye being formed from material that absorbs photonic energy emitted at the select wavelength.

10. The method of assembling a rechargeable battery of claim 1, wherein:
in said step of providing the first housing component, the first housing component that is provided contains a dye that is opaque at visible wavelengths and that is transparent at the select wavelength; and in said step of providing the second housing component, the second housing component that is provided contains a dye, the dye being formed material that is opaque at visible wavelengths and that absorbs photonic energy emitted at the select wavelength.

11. The method of assembling a battery of claim 1, wherein, in said step of providing the first housing component, the first housing component is formed from a polyphenysulfone plastic that does not appreciably interfere with the transmission of photonic energy having a wavelength that is at least one of 808 nanometers or 980 nanometers.

12. A rechargeable battery manufactured according to the steps of:
providing a first housing component, the first housing component formed from a polyphenysulfone plastic that does not appreciably interfere with the transmission of photonic energy at a select wavelength and that is formed to have an outer surface, an edge around the outer surface and an inner face that extends from the edge and that is located inwardly from the outer surface;
providing a second housing component, the second housing component formed from a polyphenysulfone plastic that absorbs photonic energy emitted at the select wavelength and that is formed to have an outer surface and a lip that extends outwardly from and is located inwardly of the outer surface of the second housing component and wherein the first and second housing components are collectively shaped so that when the housing components are placed together: the lip of the second housing component abuts the inner face of the first housing component;
placing at least one rechargeable cell in one of the housing components and connecting the cell to terminal components mounted to one of the housing components;
placing the housing components together so the lip of the second housing component abuts the inner face of the first housing component so that the first housing component surrounds the lip of the second housing component; and
directing photonic energy at the select wavelength towards the outer surface of the first housing component so that the photonic energy passes through the first housing component and is absorbed by the lip of the second housing component, so that the photonic energy heats the lip so as to cause the melting of the lip and the transfer of the thermal energy to the first housing component so as to form a weld joint along the interface between where the lip of the second housing component abuts the inner face of the first housing component so that the weld joint forms a hermetic seal between the housing components and the weld joint is located inwardly of the outer surfaces of the housing components.

13. The rechargeable battery of claim 12, further including the step of placing a pressure on the housing components so that the inner face of the first housing component and the lip of the second housing component are pressed together.

14. The rechargeable battery of claim 13, wherein said step of placing a pressure on the housing components, is performed simultaneously with said step of directing the photonic energy at the first housing component.

15. The rechargeable battery of claim 12, wherein:
in said step of providing the first housing component, the first housing component that is provided is further shaped so that the inner face is tapered; and
in said step of providing the second housing component, the second housing component that is provided is further shaped so that lip has a face surface that has a taper complementary to the taper of the inner face of the first housing component so that, as a result of said step of placing the housing components together, the tapered face surface of the lip of the second housing component abuts the tapered inner face of the first housing component.

16. The rechargeable battery of claim 15, wherein, simultaneously with said step of directing the photonic energy towards the outer surface of the first housing component, placing a pressure on one of the housing components so that tapered inner face of the first housing component and the tapered face surface of the lip of the second housing component are pressed together.

17. The rechargeable battery of claim 12, further including the step of, prior to said step of placing the housing components together, placing a microcontroller that is powered by and connected to said at least one rechargeable cell in one of the housing components.

18. The rechargeable battery of claim 12, wherein:
in said steps of providing the first housing component and the second housing component: one of the first or second housing components is provided with a reveal that is spaced from where the weld joint between the housing components is formed and that is directed to an adjacent surface of the other one of the second or first housing components; the housing components are collectively shaped so that, as a result of performing said step of placing the housing components together, the housing component on which the reveal is not formed is spaced away from the reveal; and
during said formation of the weld joint, the housing components are urged together and the abutment of the housing components is stopped by the abutment of the housing component that is not formed with the reveal against the reveal.

19. The rechargeable battery of claim 12, wherein in said step of providing the second housing component, the second housing component that is provided contains a dye, the dye being formed from material that absorbs photonic energy emitted at the select wavelength.

20. The rechargeable battery of claim 12, wherein in said step of providing the first housing component, the first housing component is formed from a polyphenysulfone plastic that does not appreciably interfere with the transmission of photonic energy having a wavelength that is at least one of 808 nanometers or 980 nanometers.

21. The rechargeable battery of claim 12, wherein:
in said step of providing the first housing component, the first housing component that is provided contains a dye that is opaque at visible wavelengths and that is transparent at the select wavelength; and
in said step of providing the second housing component, the second housing component that is provided contains a dye, the dye being formed material that is opaque at visible wavelengths and that absorbs photonic energy emitted at the select wavelength.

22. The rechargeable battery of claim 12, wherein:
in said steps of providing the first and second housing components, first and second housing components are provided that are collectively shaped so that when so that when the housing components are placed together: the lip of the second housing component abuts the inner face of the first housing component and adjacent where the lip and the inner face of the first housing component abut there is a void, the void being located inwardly of the outer surfaces of the housing components; and during said step of directing the photonic energy at the first housing component, flash formed by the formation of the weld joint flows into the void between the first and second housing components.

23. The rechargeable battery of claim 21, further including the step of, prior to said step of placing the housing components together, placing a microcontroller that is powered by and connected to said at least one rechargeable cell in one of the housing components.

* * * * *